United States Patent [19]

Liston et al.

[11] Patent Number: 4,946,651

[45] Date of Patent: Aug. 7, 1990

[54] SAMPLE HOLDER FOR A BODY FLUID ANALYZER

[75] Inventors: Max D. Liston, Irvine; Paul K. Hsei, Huntington Beach; David G. Dickinson, Glendale; George M. Daffern, Irvine; James G. Fetty, Orange, all of Calif.

[73] Assignee: SmithKline Diagnostics, Inc., Sunnyvale, Calif.

[21] Appl. No.: 194,935

[22] Filed: May 17, 1988

Related U.S. Application Data

[62] Division of Ser. No. 798,791, Nov. 15, 1985.

[51] Int. Cl.$^5$ .................................................. B01L 3/00
[52] U.S. Cl. ................................... 422/102; 220/506; 73/864.91; 422/63; 422/99; 436/43
[58] Field of Search .................... 422/102, 100, 99, 63; 206/219, 220, 221; 220/20; 141/130; 73/864.91; 436/43

[56] References Cited

U.S. PATENT DOCUMENTS

| | | | |
|---|---|---|---|
| D. 222,237 | 10/1971 | Schmit | D9/194 |
| 2,749,797 | 6/1956 | Harhs | 73/864.91 |
| 2,805,191 | 9/1957 | Hersch | 204/1 T |
| 2,851,654 | 9/1958 | Haddad . | |
| 2,902,396 | 8/1956 | Reynolds . | |
| 2,913,386 | 11/1959 | Clark, Jr. . | |
| 3,056,492 | 10/1962 | Campbell . | |
| 3,076,592 | 2/1963 | Means et al. . | |
| 3,098,813 | 7/1963 | Beebe et al. . | |
| 3,140,196 | 7/1964 | Lacy et al. . | |
| 3,208,926 | 9/1965 | Eckfeldt et al. . | |
| 3,259,301 | 7/1966 | Onasch . | |

(List continued on next page.)

FOREIGN PATENT DOCUMENTS

| | | | |
|---|---|---|---|
| 678361 | 1/1964 | Canada . | |
| 0078636A1 | 5/1983 | European Pat. Off. | 204/403 |
| 0125136A2 | 11/1984 | European Pat. Off. | 204/403 |
| 0125137A2 | 11/1984 | European Pat. Off. | 204/403 |
| 387795 | 2/1933 | United Kingdom . | |

OTHER PUBLICATIONS

Analyzers with Minature Solid Stat Electrodes (Tonetics) (1981) 2 pgs.
Video Cassette—Mock-Up of an Analyzer Device.

Primary Examiner—Michael S. Marcus
Assistant Examiner—D. John Griffith, Jr.
Attorney, Agent, or Firm—Stetina and Brunda

[57] ABSTRACT

A modular multi-channel automated medical analyzer device is disclosed, characterized by use of an ion selective electrode and/or enzymatic electrode/wash cell system which permits rapid analysis of various substances of interest contained within undiluted body fluids such as whole blood, serum and/or plasma. The ion selective electrode and/or the enzymatic electrode are disposed upon a probe which automatically axially reciprocates downwardly in a simple manipulative motion between an open-ended reference wash cell and a sample cup bearing the body fluid specimen to be analyzed. The wash cell includes an inlet port and one or more outlet ports through which is circulated an aqueous solution bearing a known concentration of the substance to be measured to provide a reference calibration medium as well as a probe washing medium. The probe is lowered directly into the sample cup to physically contact the specimen to be measured and, after analysis, is lifted upwardly into the wash cell wherein any attendant portion of the specimen remaining on the probe is stripped off by suction and the aqueous solution flow through the wash cell is initiated to thoroughly wash the probe and establish a new calibration medium for subsequent specimen analysis. The wash cell/probe assembly is specifically designed to prevent any leakage or drooling of the aqueous solution from the wash cell into the sample cup throughout manipulation of the probe. Operation of each of the modules of the analyzer is facilitated through common processing and control electronics and test measurements are accomplished initially on a dual point calibration procedure and subsequently on a single point calibration procedure.

7 Claims, 9 Drawing Sheets

Microfiche Appendix Included
(1 Microfiche, 74 Pages)

U.S. PATENT DOCUMENTS

| | | | |
|---|---|---|---|
| 3,275,534 | 9/1966 | Cannon, Jr. | 204/1 T |
| 3,294,652 | 12/1966 | Banks et al. | 204/1 T |
| 3,296,113 | 1/1967 | Hansen . | |
| 3,334,039 | 8/1967 | Vlasak . | |
| 3,365,376 | 1/1968 | Weyland | 204/1 T |
| 3,367,849 | 2/1968 | Blaedel et al. | 204/1 T |
| 3,380,905 | 4/1968 | Clark, Jr. . | |
| 3,382,105 | 5/1968 | McBryar et al. . | |
| 3,438,567 | 4/1969 | Bell, Jr. . | |
| 3,445,365 | 5/1969 | Ross . | |
| 3,479,255 | 11/1969 | Arthur | 204/1 T |
| 3,514,996 | 6/1970 | Coustau | 73/53 |
| 3,539,455 | 11/1970 | Clark, Jr. | 204/1 T |
| 3,542,662 | 11/1970 | Hicks et al. . | |
| 3,562,129 | 2/1971 | Simon | 204/296 |
| 3,575,836 | 4/1971 | Sternberg . | |
| 3,617,460 | 11/1971 | Krull et al. . | |
| 3,666,652 | 5/1972 | Krauer et al. . | |
| 3,707,455 | 12/1972 | Derr et al. . | |
| 3,712,848 | 1/1973 | Casey, Jr. et al. . | |
| 3,718,563 | 2/1973 | Krull et al. . | |
| 3,719,086 | 3/1973 | Bannister et al. . | |
| 3,776,819 | 12/1973 | Williams | 204/1 T |
| 3,799,914 | 3/1974 | Schmit | 426/85 |
| 3,838,033 | 9/1974 | Mindt et al. . | |
| 3,840,452 | 10/1974 | Baum et al. . | |
| 3,856,649 | 12/1974 | Genshaw et al. . | |
| 3,857,777 | 12/1974 | Guilbault et al. | 204/296 |
| 3,864,233 | 2/1975 | Dietrich et al. . | |
| 3,869,354 | 3/1975 | Montalvo, Jr. | 204/1 T |
| 3,911,749 | 10/1975 | Hendry . | |
| 3,919,071 | 11/1975 | Mose | 204/286 |
| 3,923,626 | 12/1975 | Niedrach et al. . | |
| 3,926,764 | 12/1975 | Ruzicka et al. . | |
| 3,926,766 | 12/1975 | Niedrach et al. . | |
| 3,930,493 | 1/1976 | Williamson . | |
| 3,957,607 | 5/1976 | Simon et al. . | |
| 3,979,274 | 9/1976 | Newman . | |
| 3,994,171 | 11/1976 | Schwartz | 73/864.91 |
| 4,115,209 | 9/1978 | Freiser et al. | 204/1 T |
| 4,172,770 | 10/1979 | Semersky et al. | 204/1 T |
| 4,179,932 | 12/1979 | Ranger | 73/864.22 |
| 4,218,197 | 8/1980 | Meyer et al. . | |
| 4,225,410 | 9/1980 | Pace . | |
| 4,284,672 | 8/1981 | Stillman | 428/35 |
| 4,310,400 | 1/1982 | Mark, Jr. et al. . | |
| 4,340,457 | 7/1982 | Kater . | |
| 4,349,429 | 9/1982 | Rhodes et al. | 204/299 R |
| 4,363,841 | 12/1982 | Snow | 428/35 |
| 4,383,451 | 5/1983 | Chapel | 73/864.41 |
| 4,387,126 | 6/1983 | Rebholz | 428/35 |
| 4,473,458 | 9/1984 | Schwartz et al. | 204/433 |
| 4,490,235 | 12/1984 | Calzi | 204/409 |
| 4,493,151 | 1/1985 | Ohyama et al. | 422/102 |
| 4,505,784 | 3/1985 | Mund et al. | 204/1 T |
| 4,512,852 | 4/1985 | Tsuboshima et al. | 204/1 T |

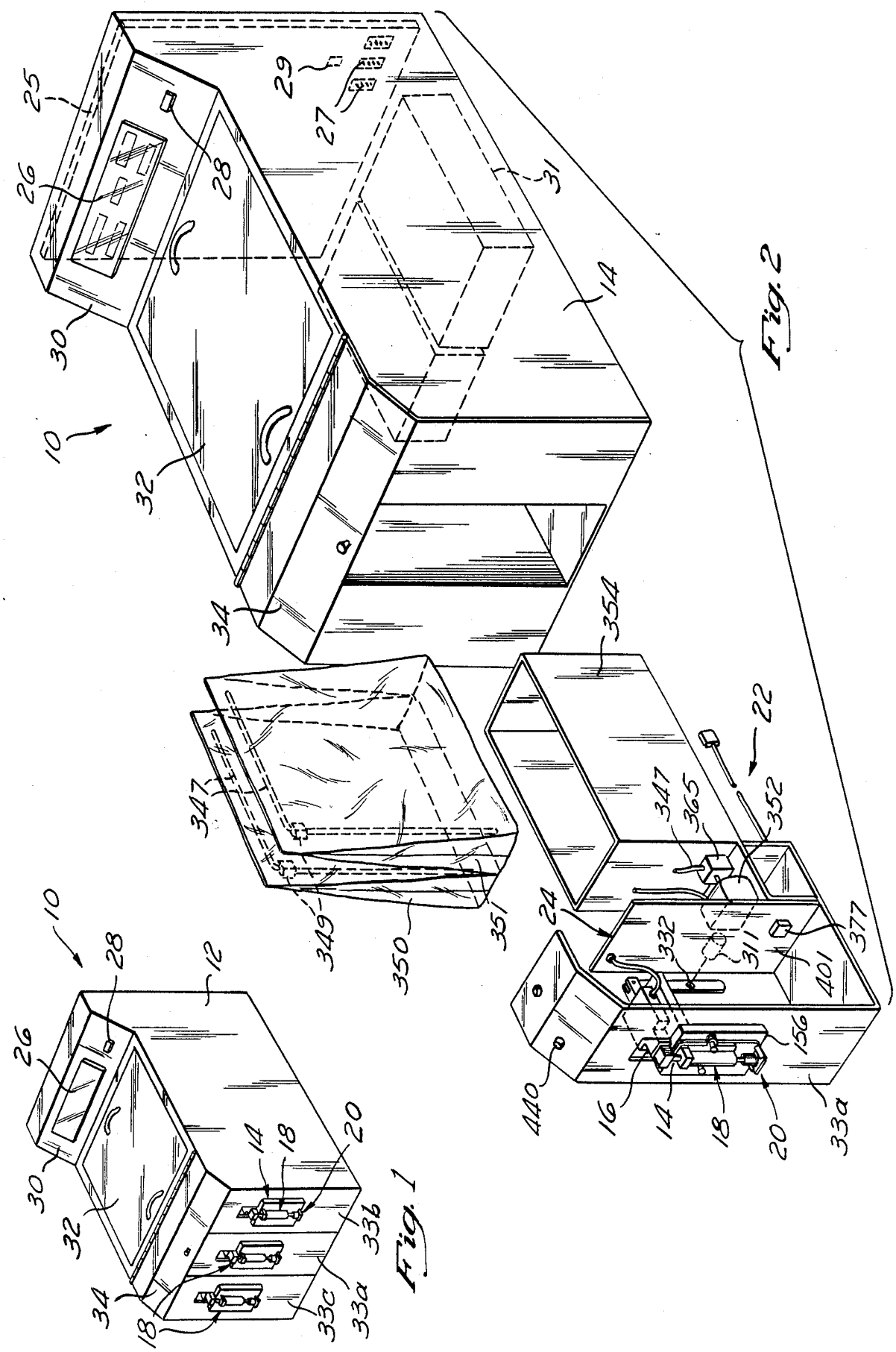

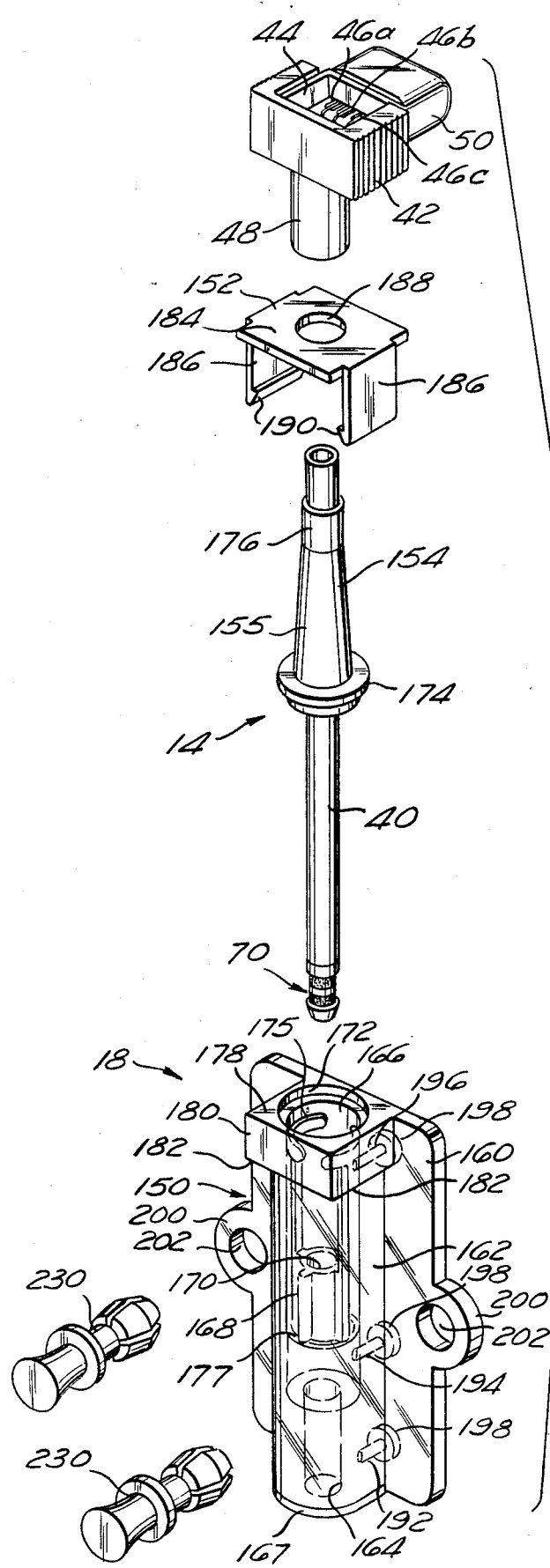
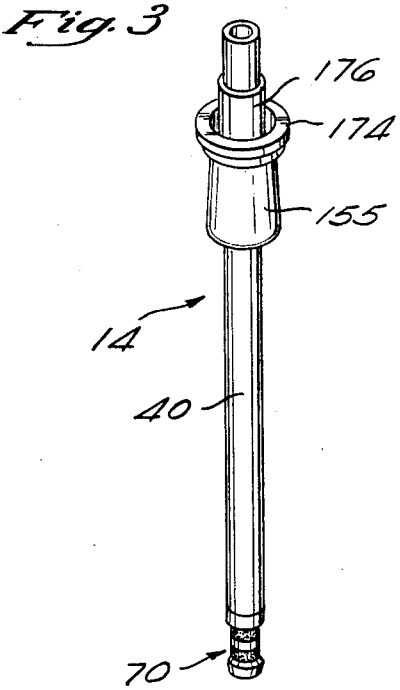
Fig. 3
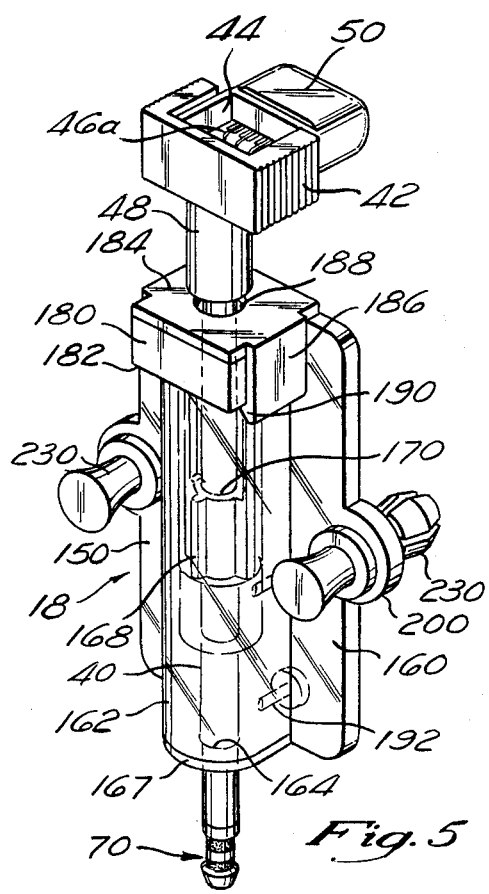
Fig. 4
Fig. 5

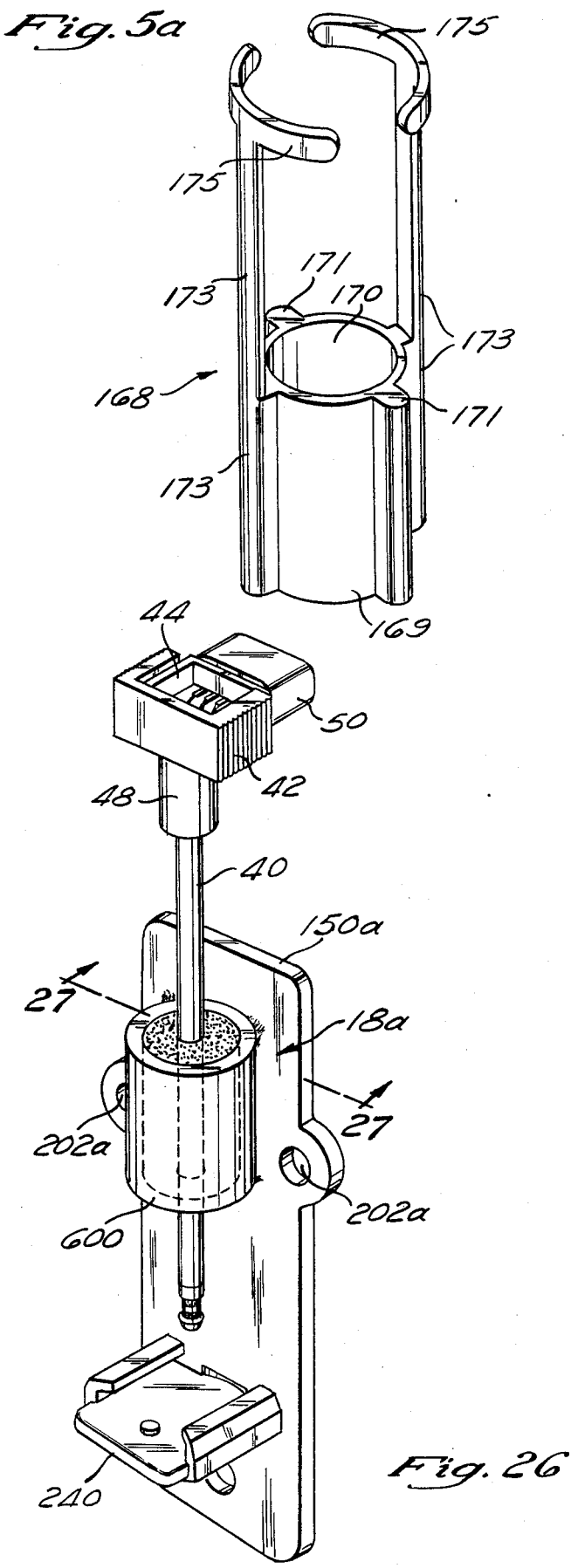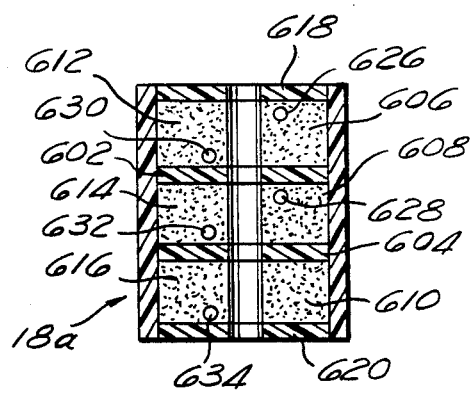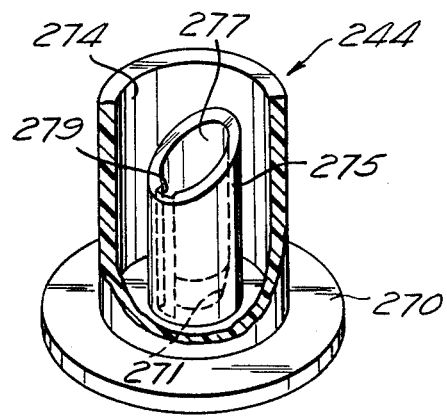

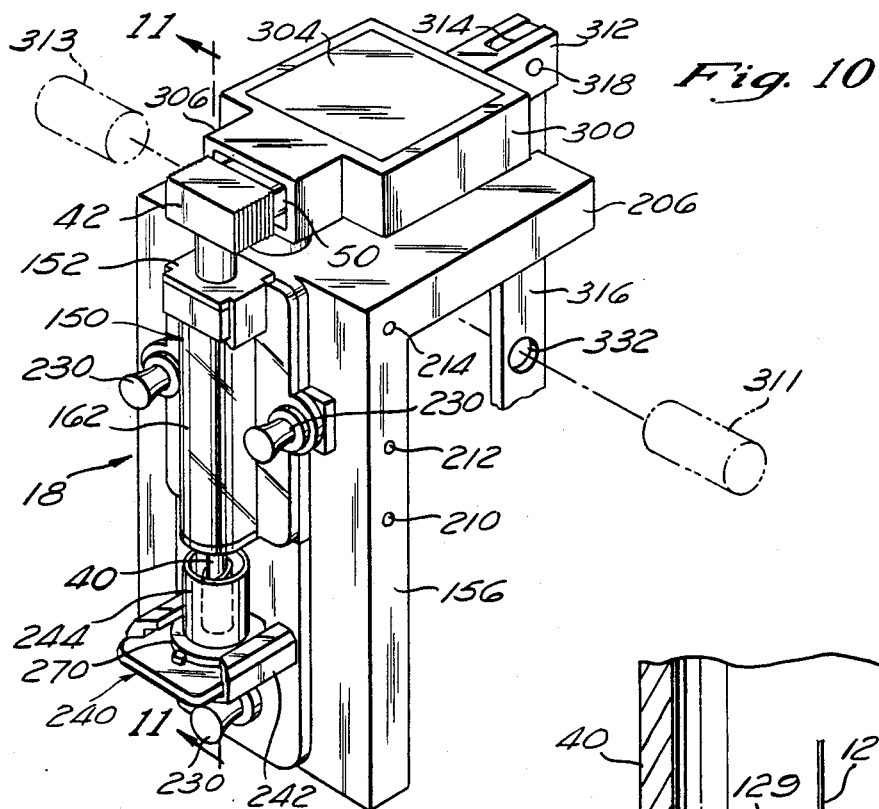
Fig. 10
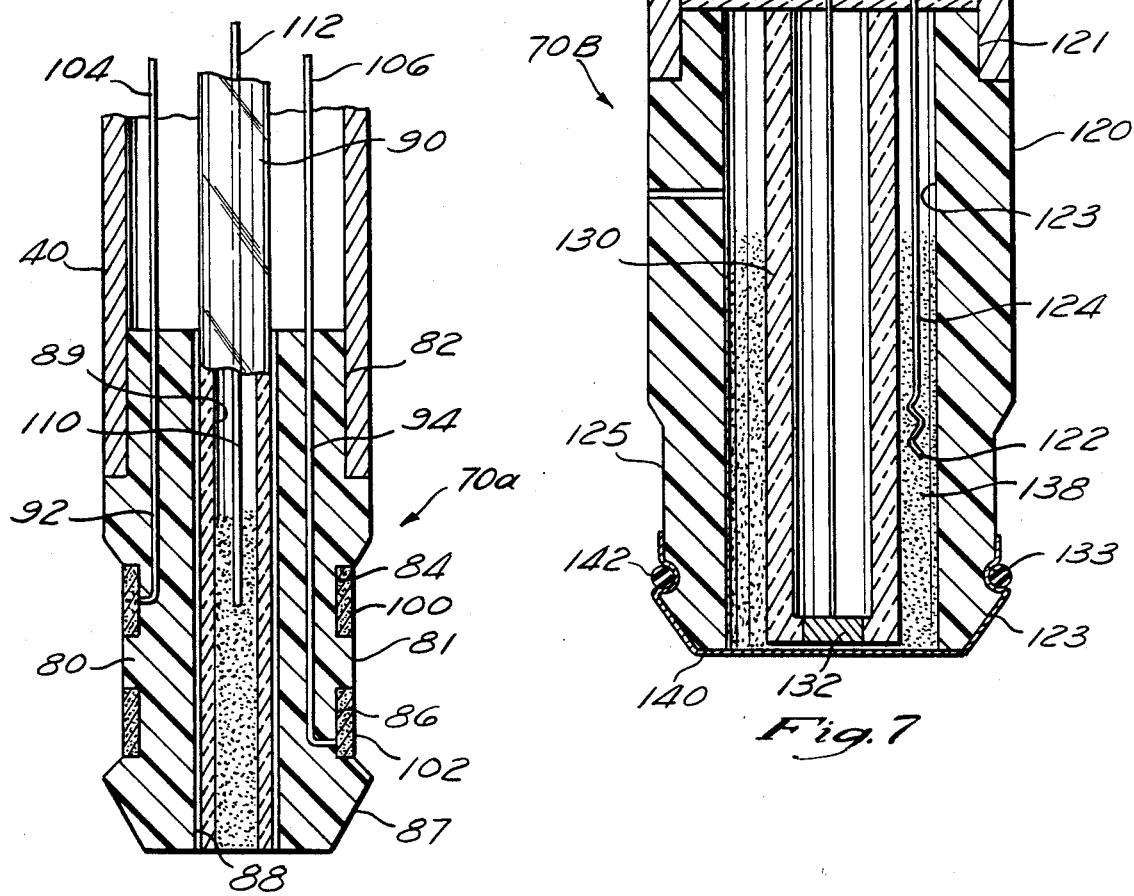
Fig. 6
Fig. 7

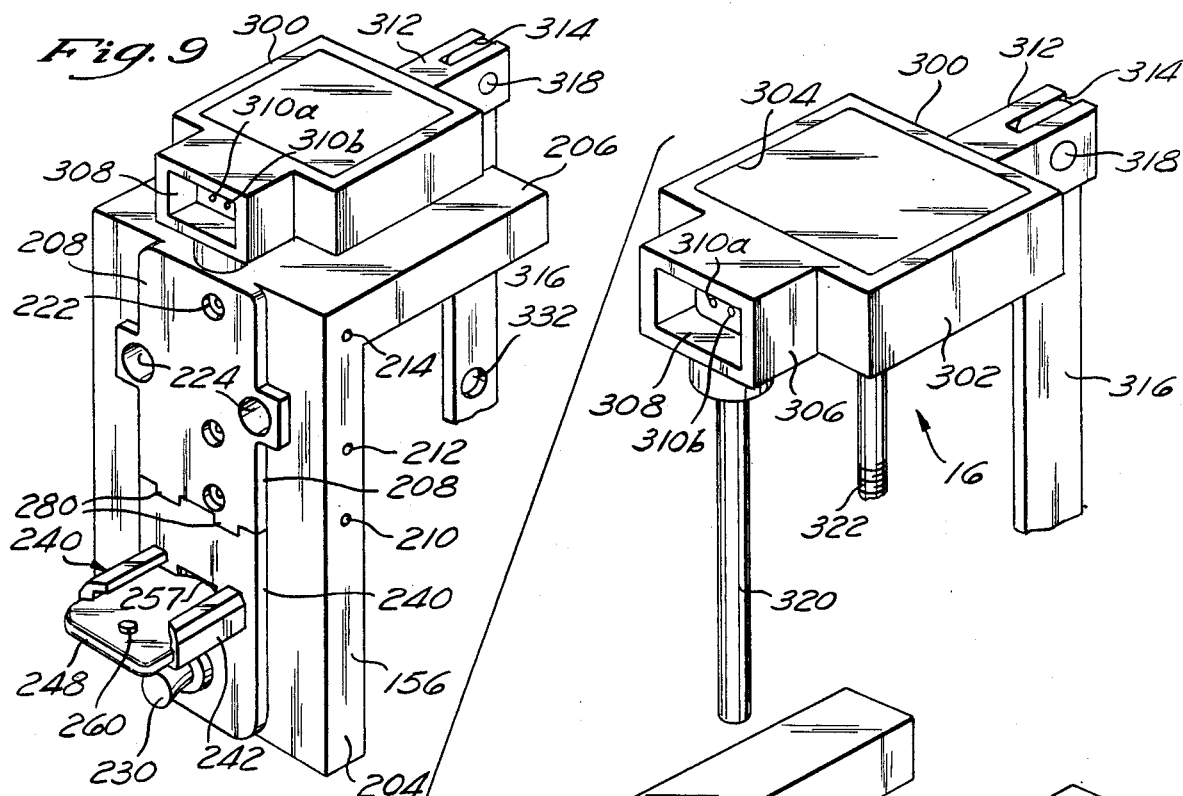
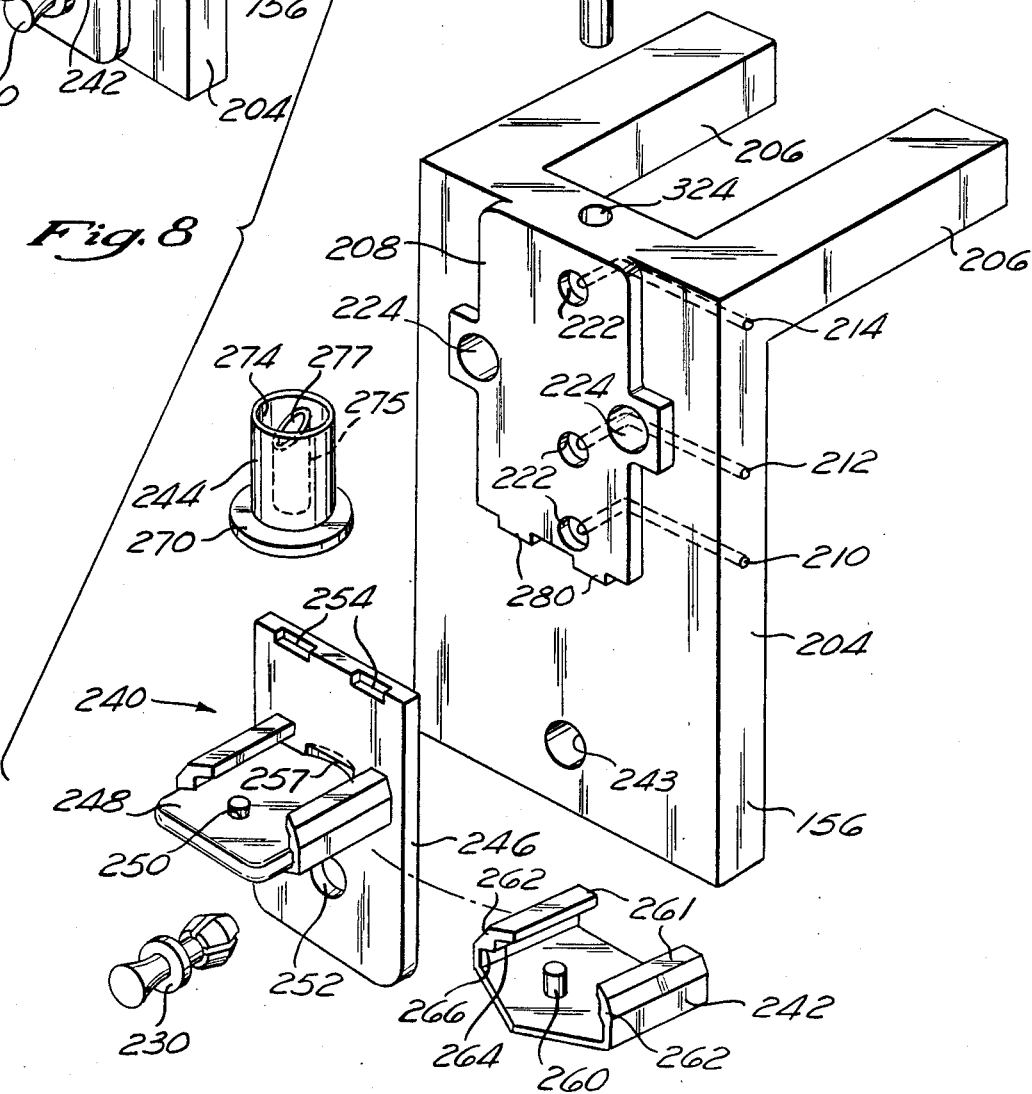

SAMPLE HOLDER FOR A BODY FLUID ANALYZER

This is a divisional of copending application Ser. No. 06/798,791 filed on Nov. 15, 1985.

This application includes a microfiche appendix including one microfiche and 74 frames.

The present invention relates generally to clinical blood analyzer devices and, more particularly, to an automated, modular, multi-channel medical analyzer device characterized by use of an ion selective electrode and/or enzymatic electrode/wash cell system which permits rapid analysis of potassium, sodium, lithium, calcium glucose, tri-glyceride, cholesterol, creatinine and other substances of interest in undiluted body fluids such as whole blood, serum and/or plasma.

As is well known, in the professional clinical treatment of patients, it is often necessary to determine the concentration of various metallic and non-metallic substances of interest in body fluids, (i.e. blood, serum or plasma) for instance, sodium, potassium, and glucose. Sodium, the major cation in extracellular fluid is a critical substance in allowing the human body to maintain proper hydration and osmotic pressure levels; and physical conditions which alter the sodium level in blood include dehydration, diarrhea and kidney malfunction. Similarly, potassium, the major cation in intracellular fluid is a critical indicator of electrolyte balance within the human body with variations in the potassium levels causing disturbances in the heart and neuromuscular systems. Additionally, glucose is a critical substance in maintaining metabolism in the body and abnormal glucose levels within the blood are indicators of hypoglycemia or serious diseases such as diabetes, which must be rapidly addressed. As such, the rapid and reliable analysis of these substances as well as other substances of interest in body fluids is absolutely necessary for proper and effective professional medical treatment.

Heretofore, it has been customary practice in the medical profession to obtain blood and/or serum analysis by sending a specimen of the same to a clinical laboratory possessing the necessary technical equipment and trained laboratory technicans required for accurate analysis. With specific reference to determining the concentration levels of sodium and potassium, traditional measurements have been obtained through flame photometry techniques while glucose determination has been typically accomplished through complicated and time consuming sample preparation and analysis techniques.

As is well known, flame photometry requires the the initial blood sample to be diluted, atomized and then burned in an air/gas environment wherein the excited molecules of interest emit a light which can be detected, processed and compared to render a resultant sodium and potassium concentration. Similarly, the various prior art laboratory preparation and analysis techniques for rendering glucose and related substances concentrations have comprised elaborate, complicated test procedures. Although such prior art laboratory, clinical analysis and measurement techniques have proven extremely reliable, due to the overall cost of the necessary test equipment, as well as the requirement for skilled technical operators to conduct the test procedures, such clinical laboratory evaluations have proven extremely costly. Further, due to the typical time delay in obtaining a body fluid sample from a patient, forwarding it to a clinical laboratory for analysis and subsequently transfering the results of the evaluation back to the medical practitioner, extremely long time delays have been commonplace which, in stat situations, have proven to be totally unsatisfactory.

In recognizing the inherent deficiencies in such prior art clinical laboratory analysis techniques, a variety of proposed analyzer systems have recently been introduced into the marketplace. Most of these recent systems have been made possible by the relatively recent introduction of a special class of ion selective ionophore materials called "neutral carrier ionophores", which have been incorporated into ion selective electrodes. Basically, such ion selective electrodes comprise an electro-chemical device which, in contact with a solution containing a sensed ion, develops an electrical potential which is logarithmically related to the concentration of that ion in the solution. Thus, by measuring this electrical potential, an accurate determination of an ion in the fluid can be mathematically derived. In addition, enzymatic electrode systems have recently been introduced wherein an organic catalyst may be utilized to convert a quantity of a desired substance to be measured into a polarographic material such as hydrogen peroxide or the like which peroxide or similar converted substance can then be measured utilizing amperometric electrode measurement techniques.

The recent prior art analyzer systems utilizing both ion selective or enzymatic electrode technology to date can broadly be segregated into two classifications; the first being manual probe systems, and the second being flow through systems. In the ion selective manual probe systems, an ion selective electrode is manually calibrated in a two point reference solution system and subsequently manually place or dipped into a test tube or vile containing a body fluid sample to be analyzed. Upon completion of the analysis, the probe must be manually washed and subsequently manually recalibrated to permit repeated analysis. An example of such a prior art manual probe system is the calcium and potassium analyzer manufactured by Ionetics, Inc. of Costa Mesa, Calif.

The flow through prior art ion selective electrode systems basically comprise an ion selective electrode which is maintained within a flow through electrode chamber through which two reference concentration solutions are sequentially pumped via an elaborate fluid conduit, valving and pumping system to permit calibration of the electrode. Subsequently, a body fluid sample is aspirated internally through the fluid conduit, valving and pump system and into the electrode chamber for measurement by the ion selective electrode. After measurement, the electrode chamber and conduit lines must be thoroughly purged and flushed for subsequent analysis applications. Exemplary prior art systems of this flow through category are the sodium/potassium analyzer model 1020 manufactured by Orion Research, Inc. of Cambridge, Mass. and the Nova 1 analyzer manufactured by Nova Biomedical of Newton, Mass. In addition, similar type flow through analyzers for enzematic electrodes have been utilized such as the Glucose Analyzer manufactured by YSI Scientific of Yellow Springs, Ohio. Although both the manual as well as flow through ion selective and enzymatic electrode prior art systems have comprised a significant improvement over the clinical laboratory techniques, they additionally have possessed inherent deficiencies which have detracted from their overall acceptance in the medical profession.

In relation to the prior art manual probe systems, the major deficiency has been the propensity of the electrodes becoming damaged upon manual entry and removal from the sample tube and during cleaning procedures thereby rendering resultant analysis data inaccurate or further requiring repeated replacement of the ion selective electrode. In addition, the major detriment of the flow through systems has been the relatively complicated and elaborate pumping and valving arrangements necessary to purge and aspirate the sample into the device which have proven to require extremely high maintenance costs and procedures. Further, due to ion selective measurements being extremely temperature dependent, both the manual probe and flow through prior systems have heretofore incorporated expensive thermostating instrumentation for reference solutions and the body fluid sample which further are prone to constant maintenance.

Thus, there exists a substantial need in the art for an improved, economical body fluid analyzer device which can be operated automatically without complicated valving and pumping systems and can be utilized by unskilled technicians to yield accurate analysis data.

SUMMARY OF THE PRESENT INVENTION

The present invention specifically addresses and alleviates the above-referenced deficiencies associated in the art by providing a modular, multi-channel automated medical analyzer device which utilizes an ion selective electrode and enzymatic electrode/open-ended wash cell system which permits rapid analysis of substances of interest, namely potassium, sodium, and glucose as well as related metals and subtances such as calcium, lithium, tri-glyceride, cholesterol, creatinine and uric acid in undilluted body fluids such as whole blood, serum and/or plasma.

With reference to the ion selective electrode, the present invention incorporates the use of a neutral carrier ionophore material dissolved in a membrane layer and positioned upon a probe which additionally includes a reference cell electrode coaxially positioned within the interior of the probe. The probe is automatically axially reciprocated from a hollow open-ended vessel termed a "wash cell" into a sample cup bearing the body fluid sample or specimen to be analyzed. An aqueous solution having a known concentration of the substanceto be measured is periodically circulated through the wash cell and one or more suction ports are provided on opposite ends of the wash cell to periodically remove a quantity of the aqueous solution at selected time intervals from the wash cell. The aqueous solution provides a reference calibration medium as well as provides a washing medium for the ion selective electrode. In addition, the wash cell/probe assembly is specifically designed to prevent any leakage or drooling of the aqueous solution from the open-ended wash cell into the sample cup throughout manipulation of the probe.

In operation, the probe is typically calibrated on a one point calibration basis within the wash cell and the probe is subsequently automatically, axially lowered directly into a quantity or specimen of undilluted body fluid contained within the sample cup. As the probe is lowered into the sample cup, the suction port located on the lowermost portion of the wash cell removes any aqueous solution remaining on the probe and thereby dries the probe prior to introduction into the sample cup. The probe is formed to include an outer metallic sleeve which has a greater thermal mass and superior thermal conductivity properties than the relatively small quantity of body fluid contained within the sample cup such that the sample and probe rapidly establish an equilibrium temperature necessary for accurate analysis purposes without the need of auxiliary thermostat temperature controls.

Analysis is rapidly accomplished by measurement of the voltage potential developed by the ion selective electrode within the sample which is then processed by way of a microprocessor to derive the concentration of the measured ion within the sample. The concentration value is then displayed on a conventional liquid crystal display. After anslysis, the probe is lifted axially upward back into the wash cell wherein the lowermost vacuum port of of the wash cell rapidly strips off any portion of the body fluid sample remaining upon the probe. The probe continues its upward axial movement within the wash cell wherein the flow of aqueous solution washes or cleans the probe and establishes a subsequent calibration medium. The device may subsequently then be utilized for additional repeated analysis applications.

In the preferred embodiment, the ion selective electrodes for two separate metal ions such as potassium and sodium are disposed upon a single probe and the aqueous solution contained within the wash cell includes a known concentration of both sodium and potassium ions whereby accurate sodium and potassium concentrations levels within the sample may be simultaneously determined. Similarly, other ion selective electrodes for related metal ion concentrations such as lithium, calcium, etc. may be utilized with analogous known concentration aqueous solutions being circulated through the wash cell.

For the measurement of non-metallic ion substances such as glucose, creatinine, tri-glyceride, cholesterol, amino acid, lactose, galactose, ascorbic acid and uric acid, the present invention utilizes an enzyme or enzymatic electrode which is positioned upon the probe and axially reciprocated in an analgous manner between the wash cell and sample cup. Basically, the enzymatic electrode comprises a glass or plastic rod sensor electrode and reference electrode system. The reference electrode is disposed within a fluid gel medium or electrolyte and is separated from the sensor electrode. A membrane is positioned to extend over the end of the sensor electrode. An organic catalyst is dissolved within and carried by the membrane which converts glucose and other related non-metallic substances desired to be measured by chemical reaction to a polarographic detectable material for instance, hydrogen peroxide which can then be measured using conventional amperometric measurement techniques. The measured current values generated by the enzymatic electrode are then converted to voltage signals which are then processed by the microprocessor to derive a glucose or other non-metallic ion substance concentration value which is displayed upon the liquid crystal display.

Due to the probe of the present invention either with the ion selective or enzymatic electrodes dipping directly into an undilluted body fluid sample in simple manipulative motion as opposed to requiring the sample to be taken internally into a flow through cell, elaborate valving and specimen sample carry over within the system are eliminated. Further, the present invention is capable of measuring very small amounts of undilluted body fluid such as fifty microliter, whereas a typical flow cell type electrode system requires a minimum of one hundred and fifty microliters of serum which is typically dilluted. In addition, due to the probe of the present invention being formed to include an outer metallic sleeve which has good thermal conductivity and a substantially greater thermal mass than the relatively small quantity of body fluid contained within the sample cup, the probe rapidly establishes an equilibrium temperature between the probe, aqueous solution and body fluid sample to ensure accurate measurements without the use of expensive thermostatic temperature controls.

In the presently preferred embodiment, it is contemplated that multiple channel or probe systems will be utilized, i.e. multiple ion selective and/or enzymatic electrode probes, on the analyzer. As such, to ensure economies in production, the present invention incorporates a unique analytical module/multiplexer processing electronics design wherein only a single central processor unit is utilized to control operation and process data for each of the multiple probe channels or modules with analysis on only one probe being permitted at one time. In addition, this modular design permits the analyzer to expand in test capability pursuant to the expanding needs of a medical practitioner as well as permit rapid maintenance and/or replacement of modules upon the analyzer.

The medical analyzer of the present invention is specifically designed to comprise a low cost reliable analyzer device which may thereby be utilized directly in the medical practitioner's office as opposed to only clinical laboratory applications. In addition, due to its automated operation, unskilled labor may easily operate the same while ensuring reliable measurement results.

DESCRIPTION OF THE DRAWINGS

These as well as other features of the present invention will become more apparent upon reference to the drawings wherein:

FIG. 1 is a perspective view showing the medical analyzer of the present invention having multiple probes disposed thereon;

FIG. 2 is an exploded perspective view of the analyzer of the present invention depicting its housing and one of the analytical modules or test stations which can be inserted into the housing;

FIG. 3 is a perspective view of the probe assembly of the present invention;

FIG. 4 is an exploded perspective view of the probe assembly in axial orientation with the wash cell assembly of the present invention;

FIG. 5 is a perspective view showing the probe assembly mounted into the wash cell of the present invention.

FIG. 5A is an enlarged perspective view of the star guide bushing removed from the wash cell;

FIG. 6 is a cross sectional view of the dual channel ion selective electrode of the present invention;

FIG. 7 is a cross-sectional view of the enzymatic electrode of the present invention;

FIG. 8 is an exploded perspective view depicting the sample cup/holder assembly, wash cell mounting plate and probe drive carriage of the present invention;

FIG. 8A is a cut-away perspective view of the sample cup of the present invention;

FIG. 9 is a perspective view depicting the sample cup holder assembly and probe drive carriage assembled upon the wash cell mounting plate;

FIG. 10 is a perspective view showing the assembled orientation of the sample cup assembly, wash cell and probe drive carriage upon the wash cell mounting plate;

FIG. 26 depicts an additional embodiment of the wash cell of the present invention; and FIG. 27 is a cross-sectional view of the wash cell embodiment of FIG. 26.

DETAILED DESCRIPTION OF THE PREFERRED EMBODIMENT

Figure 2A:
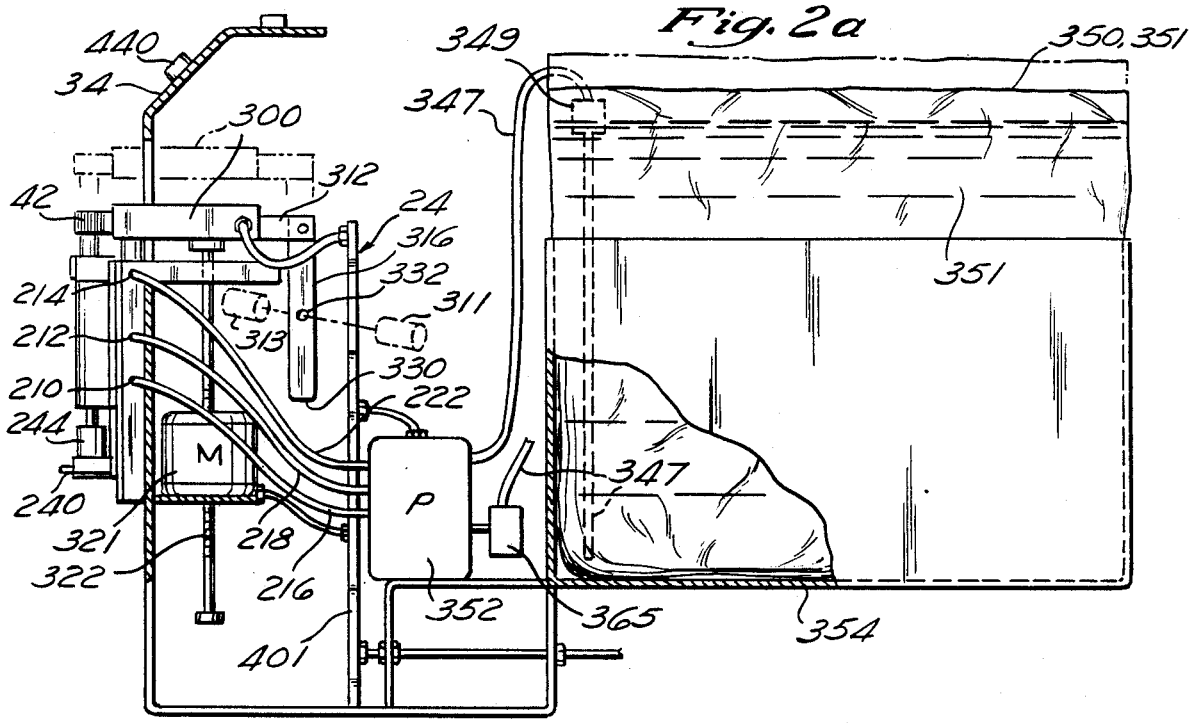
FIG. 2A is a side elevational view of one of the analytical modules of the present invention.

Referring to FIGS. 1 and 2, there is shown the ion selective/enzymatic electrode medical analyzer device 10 of the present invention composed generally of a housing 12 which supports or slideably receives one or more test stations also referred to as analytical modules, 33a, 33b and 33c. Each of the analytical modules 33a, 33b and 33c carry the major subassemblies and subcomponents of the analyzer 10 namely, a probe assembly 14, a probe drive mechanism 16, a wash cell assembly 18, a sample cup/holder assembly 20, and a fluidic pump and vacuum system 22. The operation of each of the modules 33a, b and c and thus their respective aubassemblies and subcomponents 14, 16, 18, 20 and 22 is controlled by a common processing and control electronics designated generally by the numeral 24 which is carried upon a main circuit board 25 disposed adjacent the rear of the housing 12. Each of the modules 33a, b and c are electrically connected via conventional pin connectors and multiplexed to the common processing and control electronics 24 such that the operation of all of the modules 33a, b and c can be advantageously facilitated by use of only a single microprocessor. This modular design additionally permits multiple channel probes or multiple probes to be utilized on the analyzer 10 such that multiple ion selective electrodes and/or enzymatic electrode measurements can be accomplished and, further, permits the mdoules 33 to be readily added to the analyzer 10 for replacement or to periodically expand the capability of the analyzer 10 as desired.

Although the housing 12 is depicted in FIG. 1 supporting only three modules 33a, b and c, it is presently contemplated that the common processing and control electronics 24 will facilitate the control of up to eight separate modules. In such instances, additional housings 12 will be utilized, disposed in an abutted side by side orientation and electrically connected or "daisy chained" to the main circuit board 25 as by way of more conventional multi-pin connectors or data ports 27 (schematically depicted in FIG. 2).

As best shown in FIGS. 1 and 2, the housing 12 includes a liquid crystal display 26, and a calibrate toggle switch 28 which are positioned on an inclined display panel 30. An on/off power switch 29 is additionally positioned on the circuit board 25 to be accessible from the rear of the housing 12. A removable cover panel 32 is provided upon the housing 12 to permit selective access into the interior thereof and a hinged access panel 34 is positioned adjacent the frontal surface of the housing 12. In the preferred embodiment, the housing has approximate dimensions of nine inches by fifteen inches by twelve inches and includes a D.C. power source comprising a pair of six volt batteries 31 so as to be readily portable to provide a convenient bench top analyzer for use in both clinical laboratories and medical practitioners' offices alike.

As will become more apparent infra, the interaction of the various subassemblies and subcomponents 14, 16, 18, 20, 22 and 24 designated above serve to permit the analyzer device 10 of the present invention to provide an automatic, reliable and accurate determination of the concentration of substances of interest namely sodium, potassium, and related metal ions such as calcium and lithium, etc. as well as glucose and related non-metallic substances such as creatinine, tri-glyceride, cholesterol, ascorbic acid, amino acid, lactose, galactose and uric acid contained in a sample specimen of undilluted body fluid such as whole blood serum or plasma.

As a basic overview, analysis of the specimen is accomplished by the probe assembly 14 of a selected module 33a having either an ion selective electrode or enzymatic electrode carried thereon, being axially reciprocated by the probe drive mechanism 16 between the wash cell assembly 18 and sample cup/holder assembly 20. This axial reciprocation of the probe drive mechanism 16 is controlled by the processing and control electronics 24 which additionally processes electrical signals developed by the electrode contained upon the probe assembly 14 upon immersion of the probe within the wash cell as well as the sample and outputs the concentration level of the desired substance to be measured upon the display 26. An aqueous solution of known substance concentration is periodically supplied or circulated from the wash cell via the fluidic pump and vacuum system 22 which solution provides a calibration as well as wash medium for the probe assembly 14. With this broad operational overview, a detailed description of the construction of each of the major subassemblies and subcomponents of the analyzer 10 follows.

PROBE ASSEMBLY

Referring to FIGS. 3 and 4, the detailed construction of the probe assembly designated generally by the numeral 14 is shown which as previously mentioned is disposed on each of the analytical modules 33a, b, c, etc. Basically, the probe assembly 14 comprises an elongate hollow tubular shaft or probe 40 preferably formed of stainless steel and having an approximate length of five inches and an outside diameter between 0.150 to 0.250 inches and preferably 0.190 inches. The uppermost end of the probe 40 is provided with an electrical plug connector 42 having a junction recess 44 into which the ends of three conventional electrical pin connectors 46a, 46b and 46c extend. The plug connector 42 includes a cylindrical shank portion 48 having a cylindrical bore 52 (shown in FIG. 11) extending into the junction recess 44 as well as a tang portion 50 which extends substantially perpendicularly outward from the axis of the shank portion 48. The tang portion 50 is formed having an internal recess 54 (shown in FIG. 11) into which extends the opposite ends 56a, 56b and 56c of the three pin connectors 46a, b and c. The diameter of the cylindrical bore 52 is sized to be substantially equal or slightly smaller than the outside diameter of the probe 40 such that the uppermost end of the probe 40 may be inserted into the cylindrical bore 52 and be rigidly affixed to the probe member 40 as by way of frictional engagement and/or a suitable adhesive.

The wall thickness of the probe 40 is preferrably approximately 0.050 inches such that the resultant thermal mass of the probe 40 is substantially greater than the thermal mass of the body fluid specimen sample to be measured. Due the great disparity between the thermal mass of the probe 40 and sample to be measured, as well as the good thermal conductivity properties of stainless steel, upon entry of the probe 40 into the sample, any temperature differential between the sample and the probe 40 is rapidly eliminated with the temperature of the sample quickly being equalized to the temperature of the probe 40 without the need of auxiliary thermostatic temperature controls.

Disposed adjacent the lowermost end of the probe 40 are one or more electrodes designated generally by the numeral 70 which, depending upon the particular substance desired to be measured, comprise either an ion selective electrode 70a or enzymatic electrode 70b (shown in FIGS. 6 and 7 respectively). The ion selective electrode 70a is utilized when metal ion concentrations are desired to be measured such as potassium and sodium or related metals including but not limited to lithium and calcium concentrations, while the enzymatic electrode 70b is utilized when non-metallic ion concentrations such as glucose, cholesterol, uric acid, tri-glyceride, ascorbic acid, amino acid, lactose, galactose and creatinine are desired to be measured.

Referring more particularly to FIG. 6, the ion selective electrode 70a utilized in the present invention is depicted. Basically, the ion selective electrode 70a comprises an electro-chemical device which in contact with a solution containing a sensed metallic ion, develops a potential which is logarithmically related to the concentration of that ion in the solution. This logarithmic relationship is ideally expressed by the Nernst equation:

$$E = E^0 + 2.3 RT/nF \log (pC)$$

where: E is equal to the potential developed by the the ion selective electrode in the solution; $E^0$ is equal to the potential developed by the ion selective electrode under standard calibration conditions (i.e., a constant); RT/nF is equal to the "slope" which includes the absolute temperature T and the charge with sign on the ion (n) with R and F being thermodynamic constants; p is equal to the activity coefficient of the ion in solution and C is equal to the concentration of that ion.

Thus, by knowing the various constants and constant potential $E^0$ of the Nernst equation, the concentration of a metal ion in solution can be determined by a measurement of the electrical potential E developed by the ion selective electrode 70a in solution.

In the preferred embodiment, the present invention utilizes a pair of ion selective electrodes 70a on a single probe 40 to permit the simultaneous concentration measurement of two metal ions, such as sodium and potassium within the specimen sample. As best shown in FIG. 6, the ion selective electrode 70a comprises a cylindrical polyvinyl chloride (PVC) insert 80 having a reduced diameter end portion 82 sized to be tightly received within the interior of the probe 40 and be secured thereto by frictional engagement or suitable adhesive. The lower distal end of the insert 80 is provided with an annular frusto-conical bevel 87 which assists the entrance of the electrode 70a into the sample cup 244 while the central portion of the insert 80 includes a reduced diameter portion 81. A pair of annular recesses 84 and 86 are formed upon the periphery of the central portion 81 which are axially separated from one another. An axial bore 88 extends throughout the length of the insert 80 and is sized to tightly receive an elongate tubular insert 90 preferably formed of PVC which extends axially upward throughout the length of the insert 80 and into the probe 40. A pair of apertures 92 and 94 extend radially inward from the annular recesses 84 and 86 respectively and turn axially upward extending through the upper end of the insert 80.

A neutral carrier ionophore material having a high selectivity for a particular metal ion such as the sodium ion is disposed in a suitable membrane 100 and is rigidly mounted within the annular recess 84. Similarly, a suitable neutral carrier ionophore material having a high selectivity for an additional metal ion such as the potassium ion is disposed in a membrane 102 which is rigidly mounted to reside within the annular recess 86 of the insert 80. Examples of such suitable ionophore materials and membrane constructions which can be utilized in the membrane 100 and 102 for sodium, potassium and other related metals such as calcium and lithium are well known in the art, such as that disclosed in U.S. Pat. Nos. 3,562,129 and 3,957,607 issued to Simon, the disclosures of which are expressly incorporated herein by reference.

Suitable wire conductors or leads 104 and 106 are electrically connected to the membranes 100 and 102 respectively and extend through the respective apertures 84 and 86 and the interior of the probe 40. A reference electrode 110 comprising a silver-silver chloride wire is positioned within the axial aperture 89 formed in the elongate tubular insert 90 which additionally includes a wire lead 112 extending upwardly within the interior of the probe 40. The reference electrode 110 is preferably encased in a gel substance such as Agarous which is positioned within the interior of the tubular insert 90. The three electrical leads 104, 106 and 112 extend into the interior of the plug connector 42 and are crimped and soldered to a respective one of the pin terminals 46a, 46b and 46c. As will be explained in more detail infra, the neutral carrier ionophore membranes 100 and 102 upon immersion in the aqueous solution contained within the wash cell assembly 18 and the body fluid sample contained within the sample cup assembly 20 generate an electric potential which is related to the concentration of a particular sensed ion in the solutions (i.e. the aqueous solution and body fluid sample).

Referring to FIG. 7, the enzymatic electrode 70b of the present invention is depicted which is utilized to measure various non-metallic substances of interest such as glucose, creatinine, tri-glyceride, cholesterine, uric acid, ascorbic acid, amino acid, lactose, galactose, etc. all of which in an enzyme reaction can be converted to a polarographic detectable material such as hydrogen peroxide which can then be measured by conventional amperometric techniques. As with the ion selective electrode 70a, the enzymatic electrode 70b preferrably is formed as a cylindrical insert 120 having a maximum outside diameter equal to the outside diameter of the probe 40, i.e. between 0.150 to 0.250 inches and a reduced diameter end portion 121 sized to have a diameter equal to or slightly less than the inside diameter of the probe 40 such that the same may be frictionally or adhesively retained therein. In the preferred embodiment, the insert 120 is formed of a PVC material and has an internal axial aperture 122 extending throughout its length. As with the ion selective electrode insert 80, the lower end of the insert 120 is provided with an annular bevel 123 which assists the entrance of the electrode into the sample cup 244 while the central portion of the insert includes a reduced diameter portion 125.

Coaxially disposed within the central aperture 122 is a hollow glass or PVC tube 130 which is sealingly affixed to an end cap 129 of the insert 120 and extends axially toward the lower end of the insert 120. A platinum electrode, i.e. sensor electrode 132 is carried by the hollow glass tube 130 and a suitable electrical conductor or wire lead 127 connected to the sensor electrode 132 extends upwardly through the end cap 129. A silver-silver chloride reference electrode 124 is disposed within the annular chamber 138 formed between the tube 130 and central aperture 123 and similarly includes a wire lead 131 extending axially upward through the end cap 129. The wire leads 127 and 131 extend into the interior of the plug connector 42 of the probe 40 and are crimped and soldered to the ends of a respective two of the electrical pin connectors 46a, 46b and 46c.

The lower end of the insert 120 is provided with an annular groove 133 and a thin membrane 140 extends over the lower end of the insert 120 being retained thereon by an O-ring or the like 142 disposed within the recess 133. As will be explained in more detail infra, the membrane 140 is liquid permeable and passes only relatively low molecular weight materials therethrough. The annular spaced defined between the exterior of the tube 130 and aperture 123 is filled with a suitable electrolyte which contacts both electrodes 124 and 132 which provide an electrical path between the electrodes 124 and 132. Typical electrolytes include sodium or potassium-chloride buffers including carbonate, phosphate, bicarbonate, acetates or alkali or rare earth salts or other organic buffers or mixtures. The solvent for such electrolyte may be water, glycols, glycerine and mixtures thereof. The membrane 140 carries one or more enzymes for converting the substance desired to be measured by chemical reaction into a substance which is polargraphically active. For example, the membrane 140 may be provided with a glucose oxidase enzyme which converts glucose to gluconic acid and hydrogen peroxide with the hydrogen peroxide being detectable by polargraphic techniques. In this regard, glucose being a low molecular weight material passes through the membrane 140 and reacts with the enzyme glucose oxidase carried by the membrane 140 in the presence of oxygen to form gluconolactone and hydrogen peroxide. Gluconolactone in the presence of water will hydrolize spontaneously to form gluconic acid and for all practical purposes the reaction is glucose+$O_2$, glucose oxidase, gluconic acid+$H_2O_2$.

Gluconic acid and hydrogen peroxide being relatively low molecular weight materials compared to the enzyme glucose oxidase passes through the membrane while larger enzyme molecules are retained on the lowermost side of the membrane. After a certain period of time a steady state condition is reached when the $H_2O_2$ concentration on one side of the membrane is directly proportional to the glucose concentration on the other side of the membrane. The time to reach this steady state is maintained at a minimum by maintaining the volume of the respective fluids on each side of the membrane at a minimum.

The hydrogen peroxide developed is directly proportional to the amount of glucose concentration contained in the measured sample. In addition, hydrogen peroxide readily depolarizes the polargraphic anode, i.e. the sensor electrode 132 and current flow, at a given applied voltage (usually about 0.6 volts) applied across the sensor electrode 132 and reference electrode 122 is directly proportional to the hydrogen peroxide concentration developed by the enzymatic chemical reaction adjacent the membrane 140. Basically, this proportionality is a linear relationship defined by the equation (i.e. Enzyme equation $y = mx + b$ where y is equal to the current value developed by the electrode in solution; x is equal to the current value produced by the electrode under standard calibration conditions; m is equal to the slope term and b is a constant. Thus, by measuring the current flow between the electrodes 132 and 122, developed in a aqueous solution having a known glucose concentration and the current flow developed between the electrodes 132 and 122 in the sample desired to be measured, an accurate determination of glucose concentration may be obtained.

In the presently preferred embodiment of the present invention, the current signals generated by the enzymatic probe 70b are converted to voltage signals by well known conventional techniques which voltage signals are then processed by the processing and control electronics 24. Examples of various membrane 140 constructions, enzymes, and enzymatic electrode constructions as well as measurable substances are well known in the art such as those shown in U.S. Pat. No. 3,539,455 issued to Clark, Jr., the disclosure of which is expressly incorporated herein by reference.

As will be recognized, the enzematic electrode 70b can be utilized to measure various substances of interest in a body fluid sample merely by modifying the membrane with the proper catalyst to cause the production of hydrogen peroxide or other polarographic detectable substances from substances of interest such as triglyceride, cholesterol, creatine ascorbic acid, amino acid, lactose, galactose and uric acid, as well as utilizing an appropriate aqueous solution containing a known concentration of such substances for calibration of the electrode 70b.

WASH CELL ASSEMBLY

Referring to FIGS. 4, 5, 8, 10, and 11, the wash cell assembly designated generally by the numeral 18 is depicted, which mounts the probe assembly 14 to the analyzer 10 and interfaces with the fluidic pump and vacuum system 22. The wash cell assembly 18 is composed of a wash cell member 150, probe retainer clip 152, probe roll seal 154 and wash cell mounting plate 156. As will become more apparent infra, the wash cell member 150 and probe retainer clip 152 mount the probe 40 and probe roll seal 154 for axial reciprocal movement within the interior of the wash cell member 150 while the wash cell mounting plate 156 is rigidly mounted to the front surface of each of the analytical modules 33a, b, c, etc.

The wash cell member 150 is preferrably formed of a transparent acryllic plastic material having a planar base panel 160 and a generally semi-circular shaped casing or vessel 162 integrally formed therewith. The vessel 162 includes an axial aperture 164 extending upwardly from its lowermost end, the diameter of which is sized to be slightly greater than (i.e. approximately 0.001 to 0.010 and preferably 0.002 inches) the outside diameter of the probe 40. An enlarged axial aperture 166 having a diameter approximately twice the size of the aperture 164 defines a wash and calibration chamber extending axially throughout the remaining length of the vessel 162 which is coaxially positioned with the aperture 164.

A probe guide bushing 168 (best shown in FIG. 5A) is disposed within the interior of the enlarged aperture 166 and is preferably formed of a molded plastic material. The bushing 168 includes a lower cylindrical end ring 169 having a central aperture 170 which, as with the aperture 164, has a diameter slightly larger than the outside diameter of the probe 40 to permit guided axial reciprocation of the probe 40 therethrough. Plural struts 171 and 173 preferably integrally formed with the end ring 169, are symetrically positioned along the length of the end ring 169, with the struts 173 extending axially upward beyond the end ring 169 terminating in a curvilinear shaped flange 175. The effective diameter across the struts 171 and 173 is sized to be equal to or slightly less than the diameter of the enlarged axial aperture 166 such that the bushing 168 is retained within the vessel 162 by frictional engagement. The axial position of the bushing 168 within the axial aperture 166 is fixed by abutment of the lower end of the end ring 169 against an annular shoulder 177 formed in the axial aperture 166.

An annular chamber 165 defining a vacuum chamber (shown in FIGS. 11 and 12) is additionally provided within the vessel 162 and is coaxially positioned about the aperture 164. An end cap 167 having a central aperture approximately equal in size to the aperture 164 is rigidly affixed to the lower casing 162 and defines the lower boundary of the annular chamber 165.

The uppermost end of the enlarged aperture 166 includes an annular recess 172 which is sized to receive a mounting flange 174 formed on the lower end of the probe roll seal 154. As shown, the roll seal 154 which is preferably formed of a flexible resilient elastomeric or polymer material includes a thin walled frustro-conical shaped central portion 155 extending from the flange 174 and terminating in a reduced diameter cylindrical shaped section 176. The cylindrical shaped section 176 is sized to have an inside diameter slightly less than the diameter of the probe 40 such that the cylindrical section 176 may be frictionally or adhesively affixed to the probe 40 and form a fluid tight seal thereagainst. The annular flange 174 formed on the roll seal possesses an axial thickness slightly greater than the depth of the annular recess 172 formed in the vessel 162 such that when the flange 174 is disposed within the recess 172 a small portion of the flange 174 extends slightly above the top edge 178 of the vessel 162. The upper end of the vessel 162 is additionally provided with a rectangular shaped flange 180 which extends outwardly therefrom to define a pair of abutment shoulders 182.

The probe retaining clip 152 is formed in a complementary configuration to the rectangular flange 180 and includes an upper plate portion 184 and a pair of leg extensions 186 extending perpendicularly downward therefrom. A central aperture 188 extends through the plate portion 184, the diameter of which is sized to be greater than the diameter of the probe 40 to allow axial reciprocation of the probe 40 therethrough, yet smaller than the outside diameter of the cylindrical section 176 of the roll seal 154 to prevent the roll seal from extending through the aperture 188. Each of the leg extensions 186 includes a ledge portion or tab 190 which is vertically spaced from the undersurface of the plate portion 184 through a distance slightly greater than the height of the rectangular flange 180.

Figure 11:
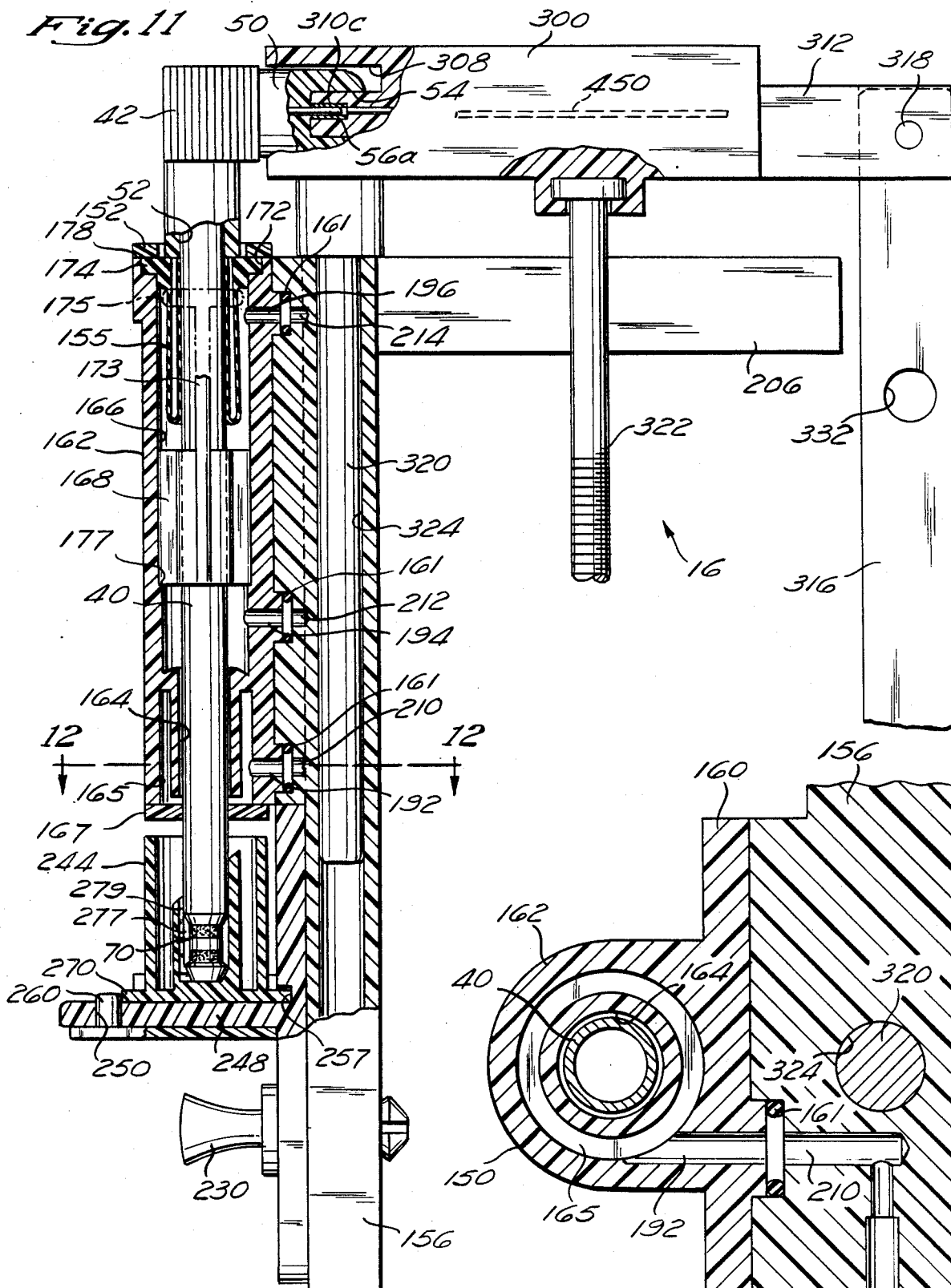
FIG. 11 is a cross-sectional view taken about lines 11—11 of FIG. 10.
Figure 12:
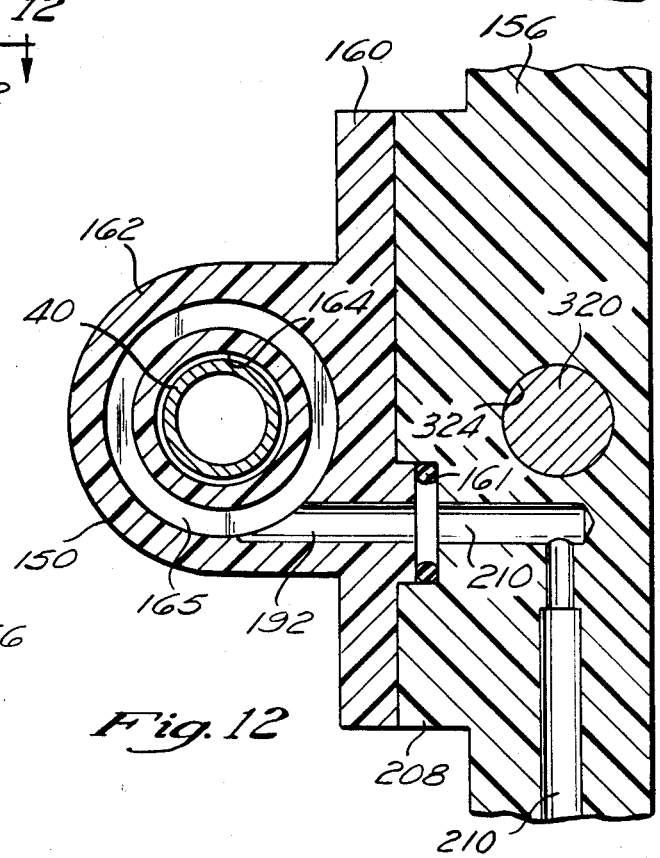
FIG. 12 is a cross-sectional view taken about lines 12—12 of FIG. 11.

As best shown in FIGS. 4 and 11, three axially spaced apertures 192, 194 and 196 extend through the base panel 160 of the wash cell member 150 and are positioned such that the aperture 192 extends into the annular chamber 165 while the apertures 194 and 196 extend into the enlarged aperture or wash chamber 166. Each of the apertures 192, 194 and 196 include an enlarged diameter boss 198 sized to compress a conventional compression O-ring seal (described infra). The base panel 160 additionally includes a pair of mounting ears 200 having a central aperture 202 formed therein which, as will become more apparent infra, permits the wash cell member 150 to be selectively mounted to the wash cell mounting plate 156.

Referring more particularly to FIGS. 8 and 9, the wash cell mounting plate 156 is formed in a generally inverted L-shaped configuration having a frontal portion 204 which is rigidly mounted to a respective analytic module 33a, 33b, 33c etc. (shown in FIG. 2) and a pair of leg extensions 206 extending substantially perpendicularly therefrom. The frontal portion 204 includes a raised boss 208 which has a configuration generally complementary to the outer perimeter of the base panel 160 of the wash cell 150. Three apertures 210, 212 and 214 initiate from the edge of the mounting plate 156 and extend through the frontal portion 204 of the wash cell mounting plate 156, the relative spacing and position of which at their intersection with the raised boss 208 are aligned to be registered with the apertures 192, 194 and 196 respectively, formed in the base panel 160 of the wash cell member 150. An O-ring recess 222 is additionally provided for each of the apertures 210, 212, and 214 upon the boss 208. A pair of mounting apertures 224 extend through the boss 208 as well as the frontal portion 204. The positioning of the apertures 224 is such to be in registry with the apertures 202 formed in the wash cell base panel 160.

The probe assembly 14 is assembled to the wash cell assembly 18 by positioning the lower end of the of the probe 40 (having an electrode 70 thereon) to extend through the probe guide bushing 168 disposed within the central aperture 164 formed in the vessel 162 and seating the flange 174 of the roll seal 154 within the annular recess 172 formed in the vessel 162. Axial downward movement of the probe 40 within the vessel 162 causes the frustro-conical shaped central portion 175 of the roll seal 154 to invert upon itself with the cylindrical portion 176 moving toward the flange 174 (as depicted in FIG. 3). The probe retainer clip 152 may then be axially reciprocated downward upon the rectangular flange 180 wherein the tabs 190 formed on the leg extensions 182 moderately flex outwardly allowing the tabs 190 to extend over the flange 180. The leg extensions 186 of the retaining clip 152 are formed having sufficient resiliency such that when the tabs 190 pass over the abutment shoulders 182 formed on the flange 180, they automatically spring inwardly to thereby retain the retainer clip 152 upon the casing member 162. Due to the flange 174 of the roll seal 154 being sized to have a height slightly greater than the depth of the annular recess 172 formed in the vessel 162, with the retaining clip mounted upon the rectangular flange 182, the under surface of the plate member 184 of the retaining clip causes a slight compression of the flange 174 against the recess 172 to form a fluid tight seal between the flange 174 and the recess 172. In addition, when assembled, the lower end of the flange 174 of the roll seal abuts the curvilinear shaped flanges formed on the struts 173 of the probe bushing 168 causing the bushing 168 to be axially fixed in position within the vessel 162 between the flange 174 of the roll seal 154 and the annular shoulder 177 formed in the axial aperture 166. As such, the roll seal provides a dynamic fluid tight seal between the probe and wash cell which permits axial reciprocation of the probe within the wash cell. Although alternative seals such as O-ring could be utilized in place of the roll seal 154, the roll seal 154 is preferred due to its reduced frictional drag properties which thereby reduces motor drive load requirements for reciprocating the probe through the wash cell 18.

With the probe assembly disposed upon the wash cell member 150, the wash cell member is mounted to the wash cell mounting plate 156 by abutting the base panel 160 against the raised boss 208 formed on the wash cell mounting plate 156. Subsequently, the mounting apertures 202 formed in the base panel 160 are aligned with the mounting apertures 224 formed on the wash cell mounting plate 156 and a pair of quick connect collet-type fasteners 230 may be extended through the aligned apertures 202 and 204 and be articulated to press the base panel 160 tightly against the raised boss 208. Such collet-type quick connect fasteners 230 are well known in the art and, hence, will not be described in any greater detail herein. As will be recognized, when the base panel 160 of the casing 162 is abutted against the raised boss 208, a slight compression of the O-rings 161 (shown in FIG. 11) disposed within the recesses 222 provides a fluid tight connection between the apertures 192, 194 and 196 formed in the base panel 160 and the apertures 210, 212 and 214 respectively, formed in the wash cell mounting plate 156.

SAMPLE CUP/HOLDER ASSEMBLY

The sample cup/holder assembly 20 is illustrated in FIGS. 8 through 11 and comprises a support shelf member 240, detent or biasing clip 242 and sample or specimen cup 244, all of which are preferably formed of a plastic material. The support shelf 240 is formed having a generally rectangular shaped base member 246 and an integrally formed shelf plate 248 which extends perpendicularly therefrom. An aperture 250 is provided in the central portion of the shelf plate 248 while a mounting aperture 252 is additionally provided in the lower portion of the base member 246. A pair of registry recess 254 are additionally formed on the upper edge of the base member 246. A small semi-circular recess 257 is provided in the base member 246 adjacent the intersection of the base member 246 with the shelf plate 148.

The detent or biasing clip 242 is formed having a generally C-shaped cross-sectional configuration and includes a central cylindrical-shaped pin or peg 260 extending perpendicularly upward from its lower surface. Each of the legs of the detent clip 242 include an enlarged head portion 262 which includes a recess channel 264 extending along its length as well as an abutment surface 266 formed adjacent its lowermost surface. The detent clip 242 is preferrably formed of a plastic material having sufficient resiliency to allow the clip 242 to be mounted upon the shelf plate 248 whereby the lower abutment surfaces 266 contact the top surface of the shelf plate 248 and the cylindrical peg 260 extends upwardly through the central aperture 250 formed in the shelf plate 248 as best shown in FIG. 9.

The sample cup 244 possesses a generally barrel-like configuration having an enlarged cylindrical base portion 270, the diameter of which is equal to or slightly smaller than the spacing between the recess channels 264 of the detent clip 242. As best shown in FIG. 8A, a central aperture 274 extends axially downward within the interior of the cup 244. A smaller cylinder 275 is coaxially positioned within the aperture 274 and includes a central aperture 277 formed having a slight conical shaped configuration sized to be slightly greater (i.e. 0.002 to 0.001 and preferably 0.003 of an inch) than the diameter of the probe 40 to serve as a reservoir for the body fluid sample to be measured. The upper end of the aperture 277 terminates axially below the end of the aperture 274 and includes an angularly inclined surface while the lower end of the aperture 277 includes a beveled annulus 271 formed in a complementary frustro-conical configuration to the beveled ends 87 and 123 of the electrodes 70a and 70b respectively. An axial groove 279 is formed in the aperture 277 extending from its inclined end and terminating at its lowermost end. The depth of the aperture 277 is preferably sized to hold a relatively small quantity of body fluid (approximately forty to seventy-five microliters and preferably fifty microliters).

When the probe 40 having an electrode 70a or 70b disposed thereon is inserted within the aperture 277, the attendant displacement of the body fluid sample upwardly within the aperture 277 spills over the angularly inclined end of the cylinder 275 and into the larger aperture 274. As such, the electrode 70a or 70b is ensured to be completely immersed within the body fluid sample. Further, due to the inclined upper end of the cylinder 274, the displaced sample spills out of the aperture 277 on only one side which additionally includes the axial groove 279 which thereby avoids any possibility of an air lock developing between the electrode 70a or 70b and permits any air bubbles accumulating on the probe to be vented via the groove 279 to atmosphere. As such, a thin film of sample (i.e. approximately 0.003 of an inch) is maintained upon the electrodes 70a and 70b upon immersion of the probe into the sample cup. In addition, the inclined upper end of the aperture 277 serves to retard any attendant wicking of the sample upward upon the length of the probe 40.

The mounting plate/shelf 240 is mounted to the wash cell mounting plate 156 and is registered relative the vessel 162 of the wash cell by engagement of the rectangular recesses 254 formed upon its upper edge with a pair of registry tabs 280 extending downwardly from the edge of the mounting boss 208. With the tabs 280 inserted within the recesses 254, a similar collet-type quick connect/disconnect fastener 230 may subsequently be inserted through the mounting aperture 252 formed in the base 246 and engaged within a complementary formed aperture 243 extending through the mounting plate 156 to thereby rigidly affix the mounting plate shelf 240 and detent clip 242 assembly to the wash cell mounting plate 156.

Referring particularly to FIG. 11, the cylindrical peg 260 of the detent clip 242 normally extends upwardly through the central aperture 250 formed in the shelf plate 248 and is positioned to be slightly above the top surface of the shelf plate 248. The insertion of the sample cup 244 upon the shelf plate 248 can be readily accomplished merely by sliding the flange 270 of the sample cup between the recess channels 264 formed on the detent clip 242 wherein the lower surface of the flange 270 contacts the peg 260 and causes the peg 260 to momentarily deflect downwardly whereby the sample cup 244 may be manually slid inwardly along the shelf plate 248 until the peripheral edge portion its flange 270 is inserted completely within the semi-circular recess 257 formed in the base member 246. Positioned in such a way, the flange 270 is spaced slightly inwardly of the aperture 250 such that the peg 260 is free to resiliently move upwardly through the aperture 250 to provide a constant biasing or detent force which prohibits improper positioning and maintains proper positioning of the sample cup 244 upon the support shelf 240. As such, it will be recognized that rapid positioning, insertion and maintenance of the sample cup within the sample holder is ensured.

PROBE DRIVE MECHANISM

The probe member 40 is axially reciprocated between the wash cell 18 and the sample cup 244 of each of the analytical modules 33a, b, c, etc. by the probe drive mechanism 16 which is depicted in FIG. 2a and FIGS. 8 through 11. The probe drive mechanism includes a carriage 300 having an enlarged rectangular central portion 302 including a rectangular shaped pocket or recess 304 which houses a probe amplifier circuit 450 (to be described infra) shown as a circuit board by the phantom lines in FIG. 11. The frontal end of the carriage 300 is provided with a rectangular extension 306 which includes a connector socket or opening 308 formed in a complementary, mating configuration to receive the tang portion 50 of the probe connector 42. Three pin terminal apertures 310a, 310b and 310c are provided within the interior of the socket opening 308 which, when the tang portion 50 of the probe connector 42 is inserted therein, electrically connect the pin connectors 46a, 46b, and 46c of the probe 40 to a respective probe amplifier 450.

A mounting strut 312 is positioned on the opposite end of the carriage 300 and includes a rectangular slot 314 adjacent its distal end. A rectangular member 316 is attached to the strut 312 by way of a fastener 318 and forms a flange extending vertically downward. A guide pin 320 extends from the lower surface of the carriage 300 and a lead screw 322 is rotatably mounted to the lowermost surface of the carriage 300 and similarly extends downwardly therefrom.

As best shown in FIGS. 10 and 11, the carriage 300 is assembled and registered to the wash cell mounting plate 156 by way of engagement of the guide pin 320 in an axial aperture 324 formed in and extending through the wash cell mounting plate 156. When assembled, the lead screw cooperates (i.e. is engaged) with a linear actuator or step motor 321 (shown FIG. 2a) which serves to selectively drive or rotate the lead screw 322 in both a clockwise and counter-clockwise direction. During rotation or movement of the lead screw 322 by the step motor, the carriage 300 is vertically reciprocated either toward or away from the mounting plate 156 with such reciprocal travel being guided by the guide pin 320 within the aperture 324. In the presently preferred embodiment, step motor 321 is implemented as a model LP221-P2, four phase step motor manufactured by Airpax, a division of North American Phillips Corporation, however, other suitable analogous or related implementation is contemplated herein.

As shown in FIGS. 2A and 10, a conventional optical sensor system comprising optical transmitter 311 and receiver 313 is mounted to each of the analytical modules 33a, b and c, etc. and are disposed on opposite sides of the flag 316 which serve to identify (i.e. confirm) the proper axial position of the carriage 300 at its uppermost and lowermost reciprocal positions, signified by the end 330 of the flag 316 and an aperture 332 located along the length of the flag member 316 respectively. As is well known, when the optical receiver 313 receives the optical beam eminating from the optical transmitter 311 (as when the beam is aligned with either the aperture 332 or distal end 330 of the flag), an electrical output signal is generated which is indicative of the desired uppermost and lowermost positions respectively of the carriage.

As will be recognized, with the carriage 300 mounted to the wash cell mounting plate 256, the probe 40 may be assembled to the carriage by insertion of the tang portion 50 of the probe connector 42 within the socket opening 308. Thus, the probe connector 42 and socket 308 form both an electrical as well as mechanical drive interface between the probe assembly 14 and the probe drive mechanism 16 and thereby throughout vertical travel of the carriage 300, the probe 40 is axially reciprocated between the wash cell 18 and the sample cup 244.

During axial reciprocation of the probe 40 between the wash cell 18 and sample cup 244, the roll seal 154 continuously rolls or inverts itself along its length forming a dynamic fluid tight seal between the probe 40 and the upper end of the wash cell chamber 166. This dynamic seal has been found to be highly preferable in wear resistance to conventional O-ring seals and, further, significantly reduces frictional resistance forces exerted upon the probe 40 during reciprocal movement as compared to conventional O-ring dynamic seals.

FLUIDIC PUMP AND VACUUM SYSTEM

Figure 2B:
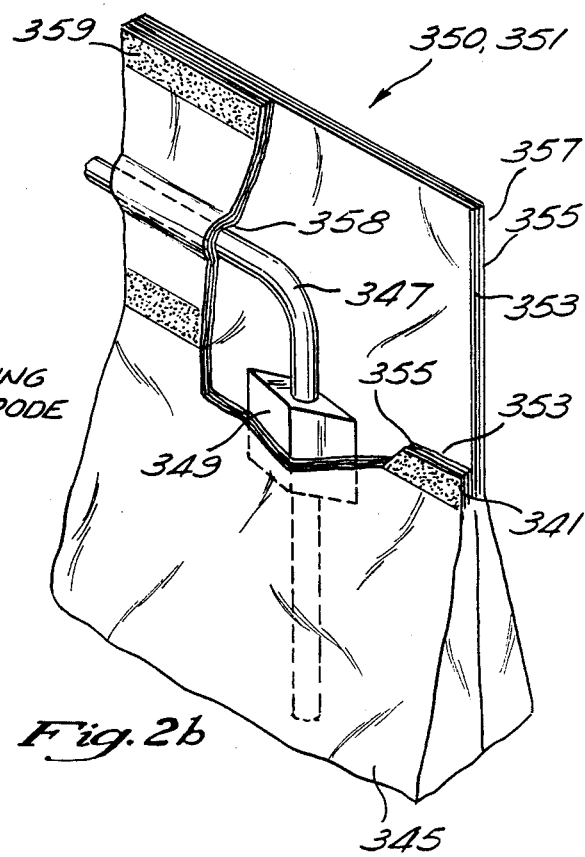
FIG. 2B is an enlarged partial perspective view of the storage reservoir utilized in the fluidic pump and vacuum system of the present invention.

The fluidic pump and vacuum system (designated generally by the numeral 22) is depicted in FIGS. 2, 2A and 2B. The fluidic pump and vacuum system is carried on each of the analytical modules 33a, b, c, etc. and is composed of a fluidic storage reservoir 350, fluidic waste reservoir 351, a pump 352 and flexible conduits 216, 218 and 222 which extend from the pump 352 to the apertures 210, 212 and 214 extending through the rear surface of the wash cell mounting plate 156. The pump 352, illustrated schematically in the Figures may advantageously comprise a multiple channel peristallic pump unit which is adapted to provide suction through the conduits 216 and 222 while providing a positive fluid displacement through the conduit 218; however, substitute analogous pumps may additionally be utilized.

Preferably, the fluid storage reservoir 350 and waste storage reservoir 351 each comprise a disposable flexible bag reservoir which are sized to be positioned in a side-by-side orientation and be carried within a reservoir housing 354 formed on the rear portions of each of the analytical modules 33a, b, c, etc. The fluid storage reservoir 350 is filled with an aqueous solution typically comprising distilled water having a known concentration of the desired substance to be measured by its respective probe 40 positioned upon the analytic module 33a, b, or c, while the waste storage reservoir 351 is initially left unfilled to provide a reservoir for spent aqueous fluid utilized in the analyzer 10. In this regard, if a sodium test is desired to be performed on analytical module 33a, the aqueous solution contained in the fluid storage reservoir 350 would comprise an aqueous solution bearing a known concentration of sodium; while if a potassium test is desired on module 33b, the aqueous solution would contain a known concentration of potassium, etc. Further, when a multi-channel electrode 70a is concentration of two substances to be measured such as potassium and sodium. Additionally, suitable anti-bacterial agents may be added to the aqueous solution to enhance storage life of the aqueous solution within the fluid storage reservoir 350, although such agents must be selected so as not to lower the surface tension properties of the aqueous solution.

In the presently preferred embodiment, the fluid storage reservoir 350 (and preferrably the waste storage reservoir as well) is formed as a multiple layer, disposable laminated flexible bag. As best shown in FIG. 2B, the outer walls of the reservoir 350 are preferably formed having a thin polyethylene liner or sheet 353 which is inert with respect to the aqueous fluid desired to be stored within the reservoir 350. A thin metallic foil layer 354 is laminated to the polyethylene liner 353 which serves to protect the stored solution from light and heat damage which could afffect the concentration of the aqueous solution contained within the reservoir. In addition, due to plastic material in general and, more particularly polyethylene, being pourous to water, the lamination of the foil layer 355 over the polyethylene liner 353 eliminates any dilution of the concentration of the aqueous solution contained within the reservoir 350. Preferably a thin layer of paper 357 is laminated on the exterior side of the foil layer 354 to permit ease in labeling or printing indicia (not shown) on the reservoir 350 to identify the contents, storage requirements, etc. of the reservoir 350.

The fluid storage reservoir is typically formed by gathering opposite sides of outer walls of the reservoir together and forming a first seal 341 (as by way of heat seal techniques) adjacent the upper end of the resevior 350 to define an interior chamber 345 located below the first seal 341. In order to permit egress and/or ingress to the chamber 345, a flexible conduit 347 is provided which extends through the first seal 341 and downwardly into the interior of the chamber 345. The conduit 347 passes through a plastic insert 349 disposed at the first seal 341 which serves to prevent crimping or blockage of the conduit 347 during the forming of the first seal 341. The length of the conduit 347 is preferably sized to extend outwardly beyond the insert by approximately six to eight inches so as to permit attachment to the pump 352 of a respective analytical module 33a, b, c, etc. However, in order to prevent any permeability of the conduit by heat or light, the free upper length of the conduit 347 is provided with an end cap and preferably disposed within a vestibule area 358 defined between the first seal 341 and a second seal 359 disposed at the upper edge of the reservoir 350. As with the first seal 341, the second seal is preferably formed by way of heat sealing techniques causing the opposite sides of the outer walls of the reservoir to be joined at a vertical elevation above the first seal 341. As such, the conduit is encased in the vestibule area (i.e. the area or region located between the first and second seals 341, 359 which thereby eliminates any diffusion of water from the reservoir through the conduit 347 during storage of the reservoir.

In order to install the fluid storage reservoir 350 upon a respective analytical module 33a, b, c, etc., a user places the reservoir 350 into the reservoir housing 354 of the analytical module and subsequently tears or cuts through the upper seal 359 of the reservoir while maintaining the first seal 341 intact. By this cutting procedure, manual access into the vestibule area of the reservoir 350 is facilitated and the free end length of the conduit 347 may be manually grasped. The end cap on conduit 347 may then be removed and the conduit 347 may be extended and connected to the inlet port of the pump 352 such that upon operation of the pump 352 a quantity of solution from the chamber 345 of the fluid reservoir 350 is delivered through the conduit 347, the pump 352, the flexible conduit 216 and into the wash cell 18. Similarly, the conduit 347 of the spent or waste fluid reservoir 351 may be connected to the discharge port of the pump 352 to allow discharge of the spent solution being pulled by vacuum from the conduits 216 and 222 from the wash cell 18 into the fluid waste chamber 345 of the waste fluid reservoir 351. Due to the spent solution being returned through the conduits 216 and 222 typically including a relatively large volume of air drawn from the annular chamber 165 and upper portion of the wash cell chamber of the flow cell 18, a conventional de-bubbler device 365 (shown in FIGS. 2 and 2A) is preferably provided between the conduit 347 and the discharge port of the pump 352 which allows the passage or venting of air to the environment prior to disposition of the spent fluid into the reservoir 351.

Due to biological considerations, the entire fluid waste reservoir 351 (as well as the fluid storage reservoir 350) may be rapidly removed from the housing 12 as by removal of the access panel 32 from the housing 12 and disposed of in a sanitary waste disposal system and, further, may be rapidly replaced in an analgous manner.

PROCESSING AND CONTROL ELECTRONICS

Figure 14C:
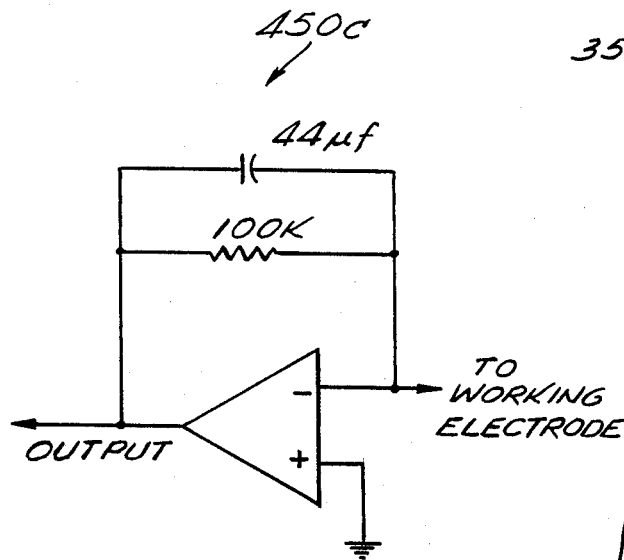
FIG. 14C is an electrical schematic of an enzymatic probe amplifier.
Figure 15:
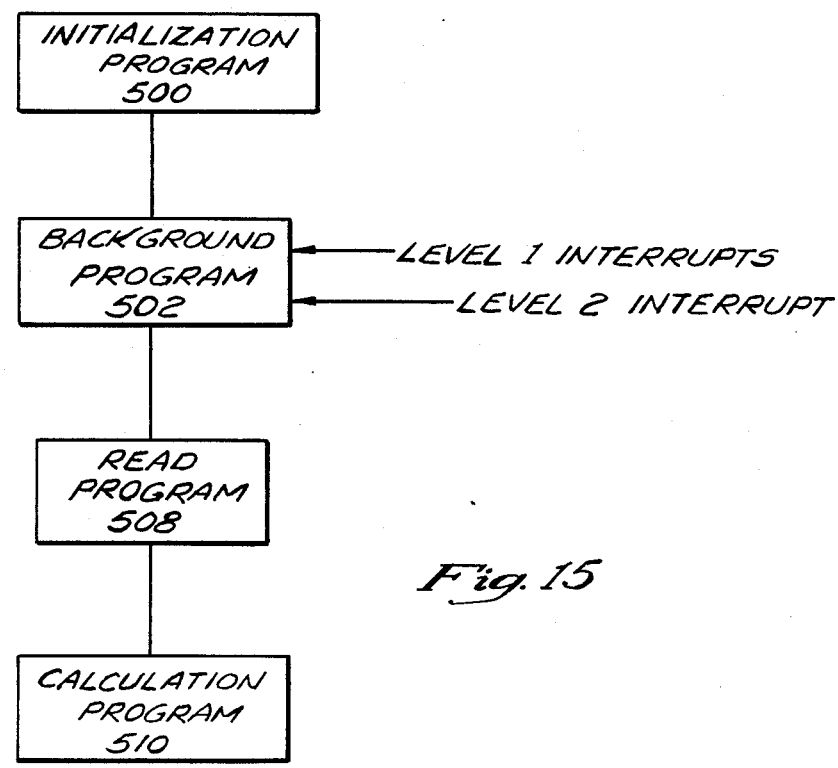
FIG. 15 is a flow chart of the main computer program of the present invention.
Figure 13:
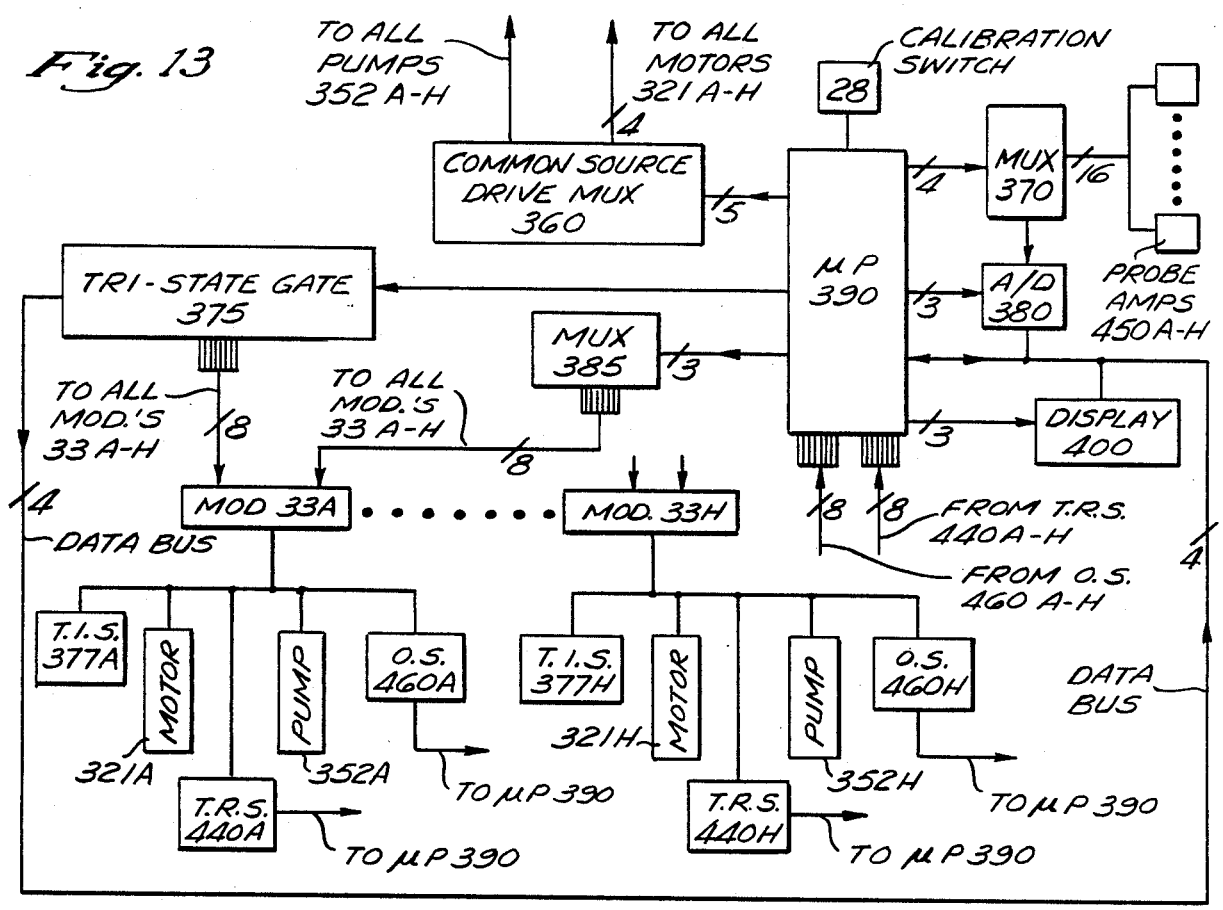
FIG. 13 is an electrical schematic of the processing and control electronics of the present invention.
Figure 14A:
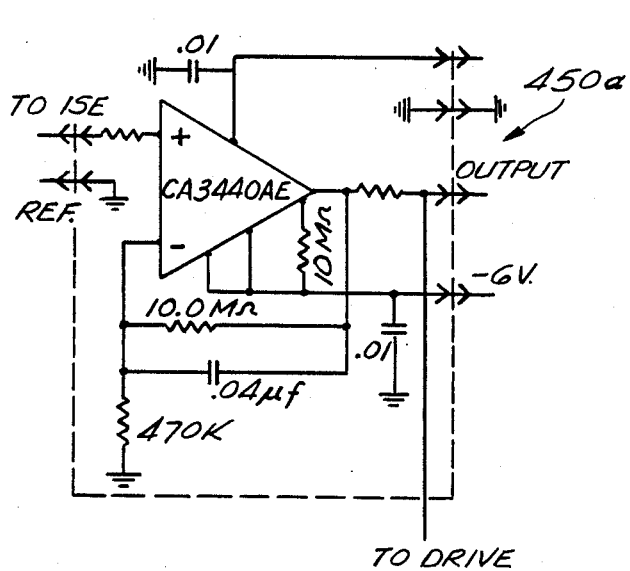
FIG. 14A is an electrical schematic of a single ion selective electrode probe amplifier.
Figure 14B:
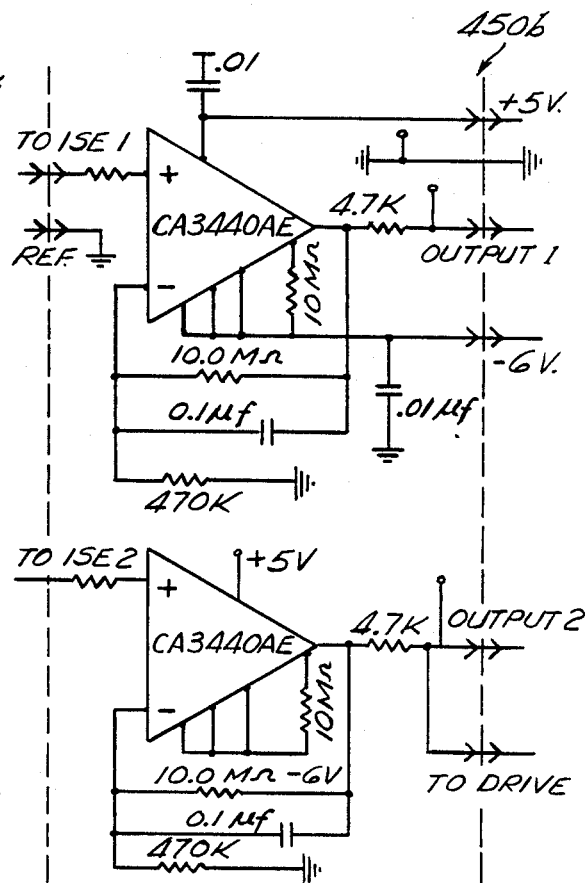
FIG. 14B is an electrical schematic of a dual ion selective electrode probe amplifier.

FIGS. 13, 14a, 14b and 14c are schematic representations of the circuitry utilized to control and monitor the operation of the analyzer 10 and, more particularly, the analytical modules 33a, 33b, etc. FIG. 15 illustrates the basic flow of the presently preferred program of operation stored in the microprocessor 390. A detailed listing of that program is set forth in the MICROFICHE APPENDIX to this specification. The control circuitry set forth at FIG. 13 is preferrably embodied in the processing and control electronics 24, which as shown in FIG. 2, are preferably disposed upon a main circuit board 25 vertically mounted adjacent the rear portions of the housing 25. The probe amplifiers 450, illustrated at FIGS. 14a, 14b and 14c, are preferrably disposed on a circuit board 450 disposed in the rectangular recess 304 of each of the probe carriages 300 (shown in phantom lines in FIG. 11) and are adapted to communicate signals between the electrodes 70a or 70b (i.e. sensing elements) on the probes 40 and the control electronics illustrated at FIG. 13.

It is to be understood that the amplifier circuits set forth at FIGS. 14a, 14b and 14c may alternatively be utilized to interface signals with the control electronics set forth. As described below, selection of a particular probe amplifier 450 is dependent upon the operating characteristics of the particular electrode/probe 40 being used on a particular analytical module 33a, b, c, etc. Other variations of the probe amplifier circuits 450a, b, and c, etc., may also be implemented within the scope of the invention in accordance with the characteristics of the particular single or dual ion selective or enzymatic electrodes 70a and 70b on the probe 40 to be employed.

Referring to FIG. 13, each probe 40 is connected to a dedicated probe amplifier 450a–h which serves to bring the signals generated from a respective probe electrode to within standardized or normalized levels preferably between plus or minus four volts. The probe amplifiers 450a–h are each adapted to communicate a signal to a multiplexer 370 in response to their operating characteristics and the test conditions of the particular probe. Multiplexer 370 is preferably implemented as a pair of multiplexers such as the model MM74HC401 and MMC4051, manufactured by National Semiconductor Corporation. The multiplexer 370 communicates to a microprocessor 390 which in the presently preferred embodiment is implemented as a model 8751 microprocessor manufactured by Intel Corporation.

The output from the multiplexer 370 is digitized by an analog to digital convertor 380 and the resultant digital information is communicated to the microprocessor 390 via a data bus for storage and interpretation. The analog to digital convertor 380 may be implemented as the model TSC7109 convertor manufactured by Teledyne. The microprocessor 390 communicates control signals to the convertor 380 to regulate the information flow between the convertor and the microprocessor. The microprocessor 390 also operates to control and communicate information to a conventional liquid crystal display 400 for viewing. The display information typically includes identification of the test being performed, results of the test and status information concerning the condition of the analyzer system.

The microprocessor 390 controls a tri-state gate 375 preferably implemented as a model no. MM70C95 tri-state gate manufactured by National Semiconductor Corporation, which communicates with each of the plural analytical modules 33a, b, c, etc. Each of the modules 33a, b, c, etc is provided with a module test identification switch 377a–h (T.I.S.) preferably mounted upon a circuit board 401 (shown in FIG. 2) disposed on each of the analytical modules 33a, b, c, etc. The test identification switches 377a–h are preferably implemented as a model number MHS-222 manufactured by ALCO Switch Company and permit the microprocessor 390 to initialize or identify the particular test analysis, i.e. operating and performance characteristics of the probe electrodes 70a or 70b disposed upon each of the analytical modules 33a, b, c, etc. This is accomplished by the microprocessor 390 being programmed (i.e. named the initialization program) to initially sequentially scan the plural test identification switches 377 through the tri-state gate 375 to read the test number from the respective test identification switch 377 which information is returned to the microprocessor via a return data bus to identify the particular test available at each analytical module. Each available test is identified by a number such as potassium being test number 1, sodium being test number 2, etc. which test numbers are subsequently stored in the memory of the microprocessor 390.

The microprocessor 390 similarly addresses a multiplexer 385 preferably implemented as a Model MM74HC4051 multiplexer manufactured by National Semiconductor Corporation, which multiplexes signals generated by activation of the plural test request switches 440a through 440h (T.R.S.) each disposed upon a respective analytical module 33a, b, c, etc. The microprocessor 390 after its initilization scan of test identification switches through the tri-state gate 375 is programmed (named the background program) to normally continuously scan the muliplexer 385 for activation of one of the test request switches 440a through 440h. When a test request switch 440a through 440h is activated, i.e. thrown, the microprocessor recognizes the same and a signal is communicated directly to the microprocessor 390 which serves to identify the particular module 33a, b, c, etc. selected for a test request procedure as well as causes the microprocessor 390 to enable a return line from the particular pump 352a-h and motor 321a-h of the selected module (to be discussed in more detail infra).

Manipulation of the probes 40 via their individual stepping motors 321a-h and operation of the associated pumps 352a-h at each of the analytical modules 33a, b, c, etc. is effected by common motor and pump drive signals which are communicated from the microprocessor 390 through a multiplexer 360 connected to each of the pumps 352a-h and motors 321a-h at the modules. The multiplexer 360 is preferably implemented as a model number MM74C906 multiplexer manufactured by National Semiconductor Corporation. The microprocessor 390 implements a predetermined pattern of movement for the motors 321 and pumps 352 to facilite programmed calibration and test operational sequences for the probes. The particular pattern of movement is determined by a subroutine accessed in the microprocessor 390 and commonly communicated to all motors 321 and pumps 352 through the multiplexer 360. The motors 321a-h are preferably implemented as four phase stepping motors such as model LP221-P2 manufactured by Airpax, while the pumps are preferably implemented as a combination supply and vacuum peristaltic pumps.

In the presently preferred embodiment, all of the pumps 352 and motors 321 at each of the analytical modules commonly receive control signals from the microprocessor 390. However, only the particular module 33 that has its pump and motor return line enabled by the microprocessor 390, via the multiplexer 385 (for instance, upon actuation of a test request switch 440), is able to respond to the signals from the microprocessor 390. In this regard, upon actuation of one of the test request switches 440a-h, the microprocessor recognizes the particular selected module and simultaneously enables a return line from the selected module motor and pump to effectuate probe and pump manipulation only at the selected module. This particular party-line enablement design permits economies in electronic components and circuitry in the analyzer. It should additionally be recognized that the present invention may accomodate different patterns of motor and pump operation by varying the subroutines stored in the microprocessor 390. Thus, the overall system has inherent flexibility to accomodate different test routines and different types of analytical modules.

The throwing of one of the plural test request switches 440 additionally causes the microprocessor 390 to recognize the particular selected module and receive signals from a particular one of the probe amplifiers 450a through 450h via the multiplexer 370 corresponding to the selected module. As will be recognized, the microprocessor 390 recognizes the source of each probe signal by its relation to a timing sequence into which information from the probe amplifiers 450 is multiplexed. Subsequently, the microprocessor 390 initiates the desired test sequence at that selected module. After a check of status conditions associated with the requesting probe (e.g. calibration due, etc.), information from the associated selected probe amplifier 450 is stored, analyzed and displayed in accordance with the particular test requirements.

The calibration switch 28 is operative to generate an interrupt to the microprocessor 390 and operates to initiate a calibration routine within the microprocessor 390. As described more fully below, the calibration routine enables a plurality of functions to allow a selected probe 40 to be moved via its respective step motor 321 to appropriate axial test positions and to facilitate contemporaneous electrical measurements. More particularly, the calibration routine enables a pattern of signals from the microprocessor to the pumps and motors of a module 33 to facilitate the desired pattern of probe movements at a particular module 33a. The calibration routine also causes the output from the probe amplifier 450 to be measured at a plurality of points during the probe movement sequence. Those measurements are then compared by the microprocessor to determine the operating characteristics of the probe and to insure that those characteristics are within predetermined limits and further to determine the slope constants for the probe which slope values are stored in memory for later calculations.

Optical sensor 460 is preferably implemented as eight redundant sensors, one disposed at each of the analytical modules. Each sensor 460 is connected to the microprocessor and is operative to generate a signal to the microprocessor 390 confirming that the position of the probe is proper, i.e. that the probe position does not deviate from predetermined limits of motion. A failure of the optical sensor at any particular analytical module to confirm proper probe positioning causes the microprocessor to abort any test sequence in process at that module.

Referencing FIGS. 14a, 14b, and 14c, alternate amplifier circuits are disclosed to accomodate signals from different types of probes. The probe amplifier circuit 450a disclosed at FIG. 14a is operative to interface a single ion selective electrode probe to the multiplexer 370. The output of amplifier 450a as with the amplifiers 450b, c, etc., is standardized to vary between desired voltage levels, preferably between plus four volts and minus four volts, in response to analog input from the probe. As previously described, enablement of the connection between a particular amplifier output and the multiplexer 370 causes an appropriate amplifier output to be recognized by the microprocessor 390.

The probe amplifier 450b, illustrated at FIG. 14b is operative to interface a probe having dual ion selective electrode probe to the multiplexer 370. Probe amplifier 450b operates in a closely similar manner as probe amplifier 450a, with the exception that only one of the two probe amplifiers illustrated at FIG. 14b has its output connected to the digital multiplexer 360.

Probe amplifier 450c, illustrated at FIG. 14c illustrates an embodiment wherein the probe amplifier interfaces the multiplexer 370 for an enzymatic electrode probe. As previously mentioned, due to the enzymatic electrode 70b of the present invention operating on amperometric measurement techniques, the analog current values obtained from the enzymatic electrode 70b are converted by conventional means to voltage signals and subsequently the converted voltage signals are standardized by the amplifier 450c and communicated to the multiplexer 370.

As previously stated, the operation of the microprocessor 390 is controlled by a series of computer programs illustrated schematically in FIG. 15. Basically, those programs comprise an initialization program 500, a background program 502, a read program 508 and a calculation program 510. Broadly speaking, the analyzer 10 of the present invention employs C-Mos programming logic which is advantageous due to its very low power requirements. The analyzer 10 is intended to be activated, i.e. turned on; and remain activated, i.e. left on; continuously such that information can be continuously stored and updated in the memory of the microprocessor 390. Basically, the stored information in the microprocessor 390 consists of a test or probe directory indicating the number and type of test available at each of the analytical modules 33a, b, etc.; a calibration due flag byte indicating whether each of the analytical modules has been recalibrated during a predetermined time period which in the preferred embodiment comprises a 24 hour period; eight calibration counters that run continuously for each of the analytical modules 33a, b, c, etc. which automatically decrement to track or log the time period remaining until the calibration due flag is set; a purge due flag byte indicating whether each of the analytical modules has been purged during a predetermined period of time which in the preferred embodiment comprises sixty minutes; and eight purge due counters which automatically decrement to log or keep track of the time remaining until the purge due flag is set.

When the analyzer 10 is initially placed into service by activation of the main power switch 29 causing the battery source 31 to be connected to the processing and control electronics 24, the initialization program 500 is initiated. In the initialization program, the microprocessor 390 initializes both the purge and calibration due flag bytes by setting the flag bytes due. The ports of the microprocessor 390, tri-state gate 375 and multiplexers 370, 385 and 360 are additionally initialized whereby the locations of each available test which is identified by a number and table of test names for each of the analytical modules 33a, b, and c is determined and stored in the test drive table memory of the microprocessor 390. As previously discussed, this initialization is accomplished by a microprocessor 390 sequentially scanning the multiplexer 385 and tri-state gate 375 and sequentially reading the module test identification switches 377 positioned at each of the analytical modules 33a, b, and c. The module test switches 377 identify the available test at the particular analytical module by a number which is then stored in the microprocessor 390. As will be recognized, with this storage, the microprocessor 390 additionally determines the location of the appropriate probe amplifier 450 associated with each analytical module 33a, b and c, etc.

The microprocessor 390 advantageously includes an internal timer interrupt which every thirty minutes generates a signal that automatically decrements each of the purge and calibration counters for the analytical modules 33a, b, c, etc. When a particular calibration or purge due counter reaches zero, it automatically sets the corresponding purge due or calibration due flag bytes.

Upon completion of the initialization program, the background program 502 is automatically initiated which comprises the normal operational routine for the microprocessor 390. In this background program 502, all interrupts are enabled, i.e. the clock interrupt, the calibration switch 28 interrupt, the test request switches 440a through 440h interrupt, all of which will be described in more detail infra. In this regard, an interrupt is required for the microprocessor 390 to leave the background program 502.

In the background program 502, the microprocessor 390 continuously sequentially scans each of the analytical modules 33a, b, etc. through the multiplexer 385 for either detection of a purge due flag set or an interrupt signal and sequentially enables the return lines for the common motor and pump drive signals for each of the modules 33a, b, c, etc. If a purge due flag is set for a particular module, the microprocessor 390 automatically turns on the pump 352 for the particular module whereby a purge of the wash cell 18 for the particular module is effectuated. In this regard, a purge of the wash cell 18 causes a new quantity of aqueous solution to be delivered to the wash cell 18 through the particular fluidic pump and vacuum system 22 of the module 33. Subsequently, the microprocessor automatically resets the purge due flag and purge counter for the particular module and reinitiates its scanning procedure.

As previously mentioned, there are various interrupts utilized in the software of the present invention. Basically there are two levels of interrupts, the highest (i.e. level 1) of which will interrupt any routine initialized by a lower level interrupt and a lower level, i.e. level 2 interrupt, which is only active to interrupt microprocessor operation when the microprocessor 390 is in its background program 502 operational mode. The highest level of interrupt on the present invention comprise the clock interrupt and calibration switch interrupt. As previously mentioned, clock interrupt is internal to the microprocessor 390 and automatically decrements the purge and calibration counters. The calibration switch interrupt is generated whenever the calibration switch 28 is manually actuated. The function of the calibration switch interrupt varies depending upon the actual program currently being implemented by the microprocessor 390. If the microprocessor 390 is in the background program 502, activation of the calibration switch interrupt sets the calibration due flag for a particular module 33a, b, c, etc. and outputs a "CALIBRATION DUE" message upon the display. If, however, a measurement test is in progress at a particular analytical module 33a, b, c, etc., i.e. the microprocessor 390 is in the read program 508, test subroutine program or calculation program 510, then actuation of the calibration switch interrupt 28 serves as a "panic button" which automatically aborts the test in progress and causes the microprocessor to return the particular probe 40 at the actuated analytical module 33a, b, c, etc. to the wash cell 18 and further causes a "READY" message to be output to the display.

The second or lower level interrupt comprise the test switch interrupt. The test switch interrupt is initiated by manual actuation of one of the test request initiated by manual actuation of one of the test request switches 440a through 440h. If actuation of one of the test request switches occurs during the progress of another test, the microprocessor 390 will ignore the same since the microprocessor 390 during a test does not scan the modules 33a through the multiplexer 385. If, however, the microprocessor 390 is in its background program 502, the actuation of one of the test request switches 440a through 440h will generate an interrupt which will be recognized by the microprocessor 390 and cause the microprocessor 390 to leave the background program 502 and initiate a test subroutine program.

In the test subroutine program, the microprocessor 390 checks the stored test drive table previously derived in its initialization program and sets the test number in the active drive register of its memory. In addition, the microprocessor 390 outputs a message to the display indicating what particular test has been selected, i.e. "POTASSIUM", "SODIUM", "CALCIUM", "GLUCOSE", etc. and whether the initial test will be to determine the concentration of such substance in an unknown sample or a calibration test. The microprocessor 390 subsequently purges the wash cell 18 of the particular module a, b, c, etc. in the manner previously described to make sure thate the aqueous solution (i.e. calibration solution) within the wash cell of the module has not been concentrated by evaporation. Upon completion of the purge of the wash cell 18 for the particular analytical module 33a, b, c, etc. the microprocessor 390 momentarily leaves the test subroutine program and calls up or initiates the read program (to be described hereinafter) wherein signals generated from the particular probe amplifier 450 of the analytical module 33 are obtained and processed.

On the return of the microprocessor 390 from the read program 508 to the test subroutine program, the microprocessor activates the pump 321 at the analytical module as well as the motor 352 at the same analytical module causing the probe 40 to travel from the wash cell into the sample cup. The microprocessor 390 additionally checks to see that the probe leaves the wash cell (designated as the "home" position), and also arrives at the proper position within the sample cup (designated as the "sample" position). This checking of the home and sample positions is accomplished by way of a respective one of the optical sensors 460a through 460h which if the optical sensor 460 does not confirm proper positioning in the home and sample positions of the probe by communicating a signal to the microprocessor 390, the microprocessor 390 outputs a "PROBE JAM" error message on the display and subsequently activates the motor 352 at the analytical module 33 and returns the probe to the "home" position. Alternatively, if the optical sensor does confirm proper probe position, the microprocessor 390 manipulates the probe by actuation of the stepping motor 352 on the selected analytical module 33 to oscillate the probe 40 up and down within the sample cup to mix the sample 244, remove any air bubbles accumulating on the probe and help establish a temperature equilibrium between the probe and the sample contained within the sample cup.

Subsequently, the test subroutine again calls up the read program 508 to obtain signals from the probe electrodes 70a or 70b within the sample cup, and upon completion of the read program further calls the calculation program 510 to be described hereinafter. Upon completion of the read program 508 and calculation program 510, the test subroutine program causes the microprocessor 390 to again activate the fluidic pump 352 of the module 33 to purge the wash cell and additionally activate the motor 321 on the module 33a to return the probe to the home position. As in the sample cup position, the microprocessor 390 preferably oscillates the probe 40 within the wash cell to complete the test subroutine.

The read program 508 causes the microprocessor 390 to enable communication between the microprocessor 390 and the particular probe amplifier 450a through 450h of the selected analytical module 33a, b, etc. through the multiplexer 370. More particularly, in the read program, the multiplexer 390 samples multiple signals generated from the amplifier 450 at multiple time intervals. Basically, these multiple readings or signal samples are spaced several seconds apart with each reading being compared with an average reading. If the reading is within predetermined tolerances, i.e. programmed into the microprocessor 390 for the particular analytical module 33a, b, c, etc. a read counter is incremented and a new reading is averaged with the previous average. If the reading is not within tolerances, the new reading is placed in an average register and the read counter is reset to zero. When the read counter reaches a predetermined value which, in the preferred embodiment comprises four readings, indicating that the four consecutive readings are within tolerance, the read program saves or stores the average reading in the memory of the microprocessor 390. In this regard, the obtaining of four running average readings within tolerance has been found by the Applicants to indicate that the probe has stablilized in its environment and that the readings therefore are valid. If, however, the probe has not reached stability after predetermined number of successive running average readings, the microprocessor 390 outputs a "READ ERROR" message to the display 400 and the test is aborted. In those instances where a dual channel probe is utilized, two separate analogous reading sequences are made for each channel of the probe electrode and stored in memory. As will be recognized, the read program 508 is called up by the test subroutine program when the probe 40 is within the wash cell 18, i.e. "home position" as well as within the sample cup, i.e. "sample position" and the operation of the read program is substantially identical in both positions. However, in the wash cell 18 or home position, the microprocessor 390 is programed to make an additional check to safeguard accuracy of the analyzer 10. This additional check causes the microprocessor 390 to compare the new average readings with the previous average obtained in the washcell 18 on the previous test. If the new average is not within predetermined tolerance of the old average, a "PURGE ERROR" message is output to the display by the microprocessor 390. Impermissable tolerances in the new and old averages is typically indicative of depletion of the aqueous solution within the wash cell, however, any form of probe instability could produce this error. With such an error, the microprocessor 390 additionally automatically sets the calibration due flag so that no results can be obtained from the analytical module 33 until the error problem is corrected.

Upon completion of the read program 508 being utilized in the sample position, the calculation program 510 is initiated. In this calculation program routine, the microprocessor 390 utilizes the readings obtained and stored in the microprocessor 390 during initiation of the read program 508 as well as the active test number stored in the microprocessor 390 from the initialization program 500 to calculate the concentration of the substance within the sample cup. In the presently preferred embodiment, the calculation program 510 comprises mathematical manipulation of the stored data in the microprocessor 390 obtained in the read program 508 and in stored memory to derive a concentration level of the substance being measured on the selected probe station.

Depending upon whether or not an ion selective electrode 70a or enzymatic electrode 70b is utilized at the particular probe station, the calculation program will either process the data utilizing the physical relationship necessitated for an ion selective electrode 70a known as the Nerst equation or for the enzymatic electrode 70b known as the Enzyme equation both of which have been previously described. The microprocessor 390 is operative to interpret the data to determine the type of electrode, i.e. either ion selective 70a, enzymatic 70b, or dual channel ion selective electrode being employed and initiate the appropriate calculation routine. Upon completion of the processing, the resultant value is output by the microprocessor 390 to the display 400 where it is visually communicated to the user. In the calculation program, if the calibration due flag byte is set, a special subroutine is preferably employed that calculates the slope of the Nerst and Enzyme equations assuming wash cell and calibrant concentrations in the stored slope tables within the microprocessor 390. This new derived slope is preferably then additionally stored in the slope table memory of the microprocessor 390 and employed in the subsequent use of the calculation program 510. In addition, the new slopes are preferrably displayed. If such slopes are marginal, a warning message is preferably output to the display. If they are outside tolerances, the microprocessor 390 automatically outputs a "BAD PROBE" message to the display and no reportable results can be obtained from the particular analytical module until a successful calibration is obtained. Upon completion of the calculation program 510, the background program 502 is automatically reinitiated such that the microprocessor 390 continues to scan the multiplexer 385 to detect activation of another test selection switch 440 interrupt or other program interrupt.

DETAILED OPERATION OF THE MEDICAL ANALYZER DEVICE

With the structure defined, the overall operation of the analyzer device 10 of the present invention can be described. From a basic overview, each of the probe stations, i.e. each of the analytical modules 33a, b, c, etc., must initially (i.e. upon first turning on the analyzer) be calibrated on a two point calibration procedure with these calibration values being stored in the microprocessor 390. Subsequently, repeated test analysis is facilitated through a one point calibration procedure initiated through the test subroutine program which permits rapid response and accurate results until such time as calibration is required by software operations discussed above. The sequence of probe movements for both the calibration as well as the subsequent test routine for each station upon the analyzer 10 is substantially the same and is schematically depicted in FIGS. 16 through 25 inclusive.

To initiate the initial two point calibration sequence, a sample cup 244 is manually filled with a quantity of a solution bearing a known concentration of the particular substance desired to be measured at the probe station, such as potassium, sodium, glucose, etc. Preferably, the concentration of this calibrant solution is proximal but differing to the same substance concentration of the aqueous solution stored in the storage reservoir 350 of the respective analytical module 33a of the probe station. The filling is accomplished by placing approximately 40 to 75 microliters of the calibrant solution within the central aperture 277 of the sample cup 244. The filled sample cup 244 may then be positioned upon the particular respective probe station sample cup assembly 20 in a manner previously described to register the cup 244 with the probe 40 of the respective probe station. Subsequently, a user merely turns on the analyzer 10 by way of a manual power switch 29 which causes the processing and control electronics 24 to run through its initialization 500 and background 502 programs in a manner previously described. Since at initial activation of the analyzer cell calibration due flags are set, upon actuation of the respective test request switch 440 for the particular desired probe station on an analytical module 33a, 33b, etc., a "CALIBRATION DUE" message is automatically displayed upon the liquid display 400 and the microprocessor causes the particular step motor 321 of the selected probe station to be activated and axially raise the probe carriage 300 and, more particularly, the probe 40 upward to the "home" position indicated in FIG. 16, i.e. with the lower end of the probe 40 being disposed at the transition between the wash chamber 166 and vacuum chamber 165 of the wash cell 18.

To initiate the calibration procedure, the user manually toggles the calibration switch 28 located on the inclined display panel of the housing of the analyzer 10, whereby the microprocessor 390 causes a "CALIBRATION" message to be output to the display 400. The respective test request switch 440 for the particular desired probe station or analytical module 33 must then again be manually activated. The wash chamber 166 is then immediately purged with a quantity of the aqueous solution having a known concentration of the substance to be measured, i.e. sodium, potassium, glucose, etc. at the partition module 33a, b, c, etc. by activation of the probe station pump 352 via the common pump drive 420 which causes aqueous solution to be drawn from the particular fluid storage reservoir 350 at the module and be supplied to the inlet port 194 of the wash chamber 166 via the pump conduit 218 and aperture 212 formed in the wash cell mounting plate 156. Simultaneously, the pump 352 draws a vacuum through the pair of conduits 216 and 222 connected to the respective apertures 210 and 214 formed in the wash cell mounting plate 156 which is communicated to the vacuum ports 192 and 196 of the wash cell. This vacuum serves to remove the spent aqueous solution presented at the annular vacuum chamber 165 wherein it is returned to the waste reservoir 351 of the particular module 33 via the conduits 216 and 222 and de-bubbler device 365. In this manner, the wash cell 18 is purged with the quantity of known concentration aqueous solution being circulated through the wash chamber 166, downwardly through the aperture 164 and subsequently through the vacuum chamber 165. The purge thereby ensures that the wash cell 18 holds or maintains a sufficient quantity or column of aqueous solution after completion of the purge cycle.

The upper vacuum port 196 of the wash cell 18 mainly removes any trapped air accumulating within the upper region of the wash chamber 166 and nearly all of the aqueous solution entering into the wash chamber 166 travels downward by gravity flow through the aperture 164 toward the vacuum chamber 165 opening wherein it is aspirated circumferentially outward and through the vacuum port 192. In this regard, the vacuum chamber 165 is designed to remove the aqueous solution traveling downwardly within the aperture 164 of the wash cell at a rate equal to the rate at which the solution is supplied to the wash chamber 166 so as to prevent any solution from traveling through the lowermost opening 167 of the wash cell. Further, although in the preferred embodiment a pair of vacuum ports are utilized in the wash cell, those skilled in the art will recognize that only one vacuum port is required for this purpose.

In addition, it is an extremely important and novel feature of the present invention that in order to rapidly manipulate the probe 40 between the wash cell 18 and the sample specimen contained within the sample cup, it is necessary in the presently preferred configuration of the present invention to have a wash cell or vessel that has a closed upper end and open lower end and which does not drool or drip the aqueous solution into the specimen sample cup. This is accomplished in the present invention by the novel design of the wash cell 18 and probe assembly 14 in combination with the fluidic pump and vacuum system 18 on each module 33 to take advantage of natural surface tension characteristics of an aqueous solution. More particularly, the applicant's have found that by limiting the size of the aperture life 164 to be between 0.050 to 0.250 inches, the surface tension properties of the aqueous solution can be utilized such that the aqueous solution forms an inverted meniscus at the lower open end or opening 167 of the wash cell 18 when the probe is in the wash cell. The meniscus is formed by the surface tension properties of the aqueous solution which when the solution is maintained in the wash cell having a closed upper end and open lower end, atmospheric pressure acts upwardly upon the solution through the lower open end to support the inverted fluid meniscus. In addition, any drooling of the aqueous fluid during reciprocation of the probe through the meniscus is eliminated by the close tolerance of the probe diameter 40 with the opening 167 which in the preferred embodiment comprises a probe diameter of 0.191 inches with the opening 167 being 0.203 inches in diameter. Further, so as not to disturb the formation and maintenance of the inverted meniscus when the probe is disposed within the wash cell, the annular configuration of the vacuum chamber 165 serves to remove solution from the aperture 164 adjacent the opening 167 radially outward.

Subsequently, the operation of the pump 352 and step motor 321 is discontinued and voltage readings from the probe amplifier 450 generated by the probe electrode 70 within the calibrant aqueous solution maintained within the wash cell are taken. Discontinuance of the motor 321 and pump 352 operation eliminates any transient noise being introduced into the probe readings. As more particularly described supra, pursuant to the read program commands, four consecutive readings are taken with the averaged reading being maintained in the memory of the microprocessor 390. Upon completing the probe electrode reading sequence, the pump 352 and motor 321 are again activated and the probe 40 is reciprocated downward from the wash chamber 166 and toward the vacuum chamber 165 as depicted in FIG. 17.

Figures 16, 17, 18, 19, 20:
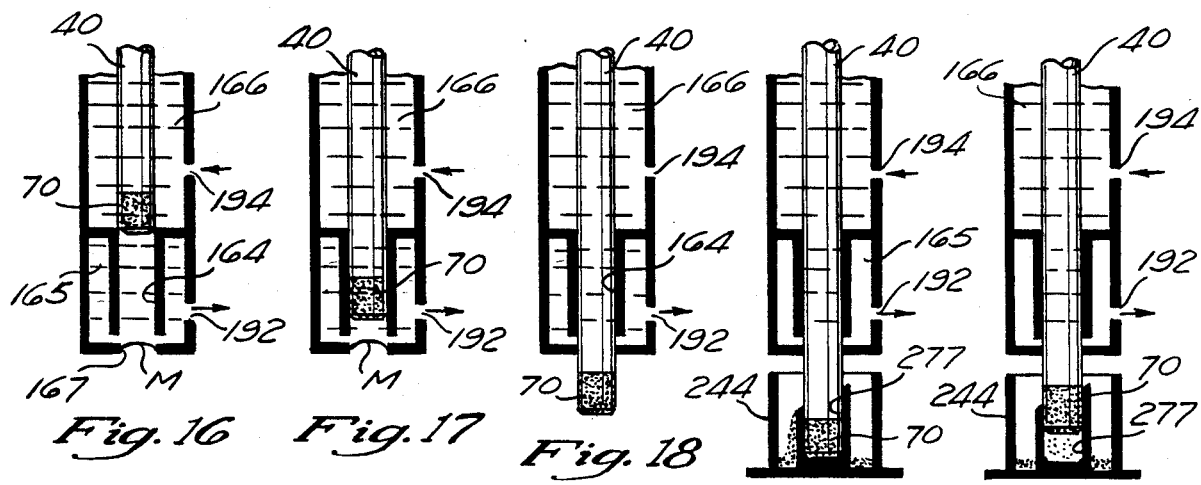
FIGS. 16 through 25 are schematic views illustrating the sequential steps of the probe during a calibration and/or test routine.

Continued downward axial movement of the probe 40 causes the end of the probe to extend through the inverted meniscus M and additionally travel past the circumferential opening of the vacuum chamber 165 wherein any solution adhering to the probe 40 is completely stripped off and aspirated through the outlet port 192 as depicted in FIG. 18. Due to the velocity of air being aspirated through the outlet port, the end of the probe 40 is additionally thoroughly air dried following passage through the opening 167. Continued axial movement causes the end of the probe 40 to enter into the second calibrant solution maintained within the sample cup 244 as depicted in FIG. 19.

As schematically depicted in FIG. 19, entry of the end of the probe 40 into the central aperture 277 of the sample cup 244 is assisted by the frustro-conical shaped bevel 87 or 123 (shown in FIGS. 6 and 7) of the ion selective electrode 70a and/or enzymatic electrode 70b respectively. Continued downward motion of the probe 40 causes the calibrant solution within the aperture 277 to displace upwardly spilling over the angularly inclined end of the aperture 277 and into the annulus formed between the outer cylindrical wall 275 and inner cylindrical wall of the sample cup 244. In the preferred embodiment, the diameter of the aperture 277 is approximately 0.002 through 0.010 inches and preferably 0.003 inches greater than the outside diameter of the probe such that the calibrant solution contained within the aperture 277 forms a thin film coating throughout the length of the electrode thereby ensuring that the electrode 70 is completely immersed within the solution. It will further be recognized that due to the configuration of the electrodes 70a and 70b of the present invention maintaining the electrode membranes upon a reduced diameter portion of the electrode inserts, direct contact of the membranes 100, 102 and 140 with the side walls of the aperture 277 of the sample cup 244 is eliminated which has been found to substantially prolong electrode life.

Figures 21, 22, 23, 24, 25:
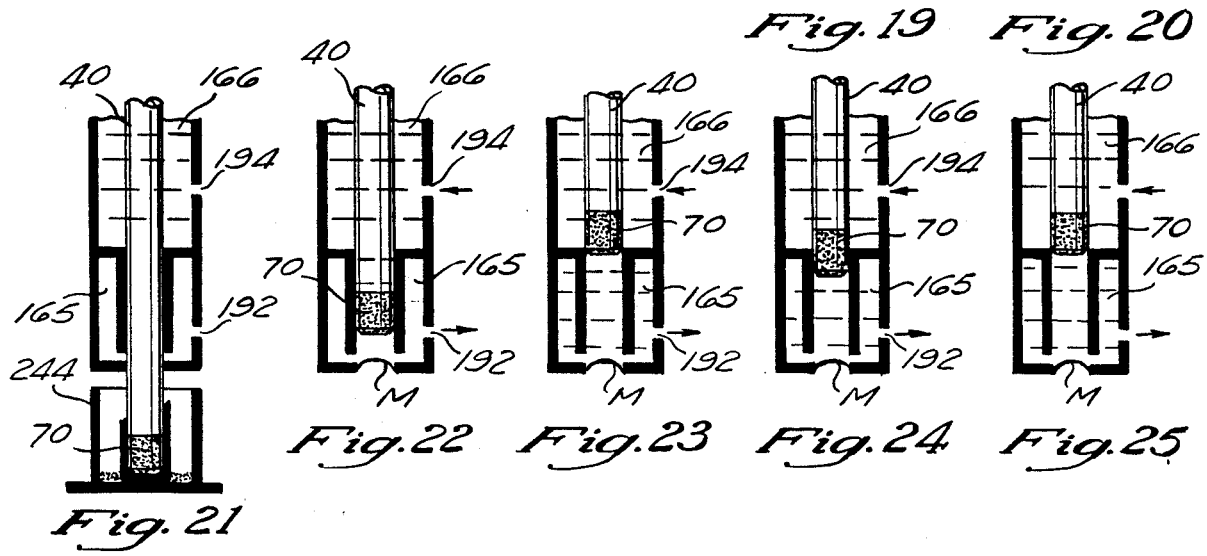

To ensure that air bubbles are not present upon the electrode 70 within the sample cup 244, the probe 40 is vertically oscillated, i.e. bobbed up and down through a short distance within the sample cup by sequential up and down actuation of the probe motor 321 (as depicted in FIGS. 20 and 21) and subsequently remains at its lowermost position shown in FIG. 21 wherein the pump 352 and step motor 321 operation are again discontinued. During this oscillation any air bubbles present on the probe migrate to the axial channel 279 formed in the aperture 277 of the sample cup 244 are freed to be vented to the atmosphere. With the electrode 70 disposed in the sample cup, an additional four readings are obtained from the amplifier 450 of the probe 40 which are processed and stored in the memory of the microprocessor 390.

The pump 352 and step motor 321 operations are then again initiated causing the probe 40 to be axially reciprocated upward from the sample cup 244 and back into the wash cell 18, i.e. "home" position. As the lower end of the probe 40 passes across the opening of the vacuum chamber 165, the inverted meniscus is automatically reformed by solution surface tension and the major portion of any attendant quantity of sample remaining on the probe 40 is stripped off from the probe 40 and aspirated through vacuum port 192 as depicted in FIG. 22. The probe 40 subsequently continues upwardly to the position illustrated in FIG. 23 wherein it is positioned within the wash chamber 166. To ensure proper cleaning of the probe 40, the probe 40 is then axially oscillated or bobbed up and down (as represented in FIGS. 24 and 25) whereby a thorough washing of the electrode 70 is completed with any remaining portion of the sample on the probe being carried off by the aqueous solution being simultaneously circulated through the wash chamber 166. As will be recognized therefore, the aqueous solution in the wash cell 18 serves as both a calibrant as well as probe wash medium.

Pursuant to the calculation program commands, the read values or signals obtained and stored in the microprocessor memory in this initial two point calibration (i.e. in the wash cell 18 and the sample cup 244) are then processed by the microprocessor 390 to render a slope term for either the Nertz or Enzyme equations (i.e. depending whether an ion selective electrode 70a or enzymatic electrode 70b is utilized on the particular probe station) which slope term is then stored in the memory of the microprocessor 390 for later use in slope comparison and testing calculations. As such, initially, a two point calibration is provided with to known concentration calibrant solutions, i.e. the first point being within the wash cell chamber and the second point being in the sample cup. Once the two point calibration has been completed for the probe station, (and similarly for the other remaining probe stations) successive or repeated actual test sequence can be selectively initiated on the calibrated probe station which as explained below, only utilizes a single point calibration system.

To initiate a desired test or measurement procedure upon the analyzer 10, a body fluid sample such as blood, serum or plasma sample must be extracted from a patient in a conventional manner and inserted into an additional sample cup 244 in the manner previously described. The sample cup is positioned upon the sample cup assembly 20 of the desired probe station (i.e. analytical module 33a, b, c, etc.) to be utilized and is similarly registered therewith by the sample cup detent mechanism. The test request switch 440 for the particular probe station is then subsequently manually toggled causing the test subroutine to be initiated upon the microprocessor 390. The identical manipulative steps of the probe 40, pump 352 and step motor 321 previously described in relation to the calibration procedure and illustrated in FIGS. 16 through 26 are then sequenced resulting in the read signals of the electrode derived in the wash cell 166 (i.e. single calibration values) being stored in the microprocessor's memory as well as the read signals of the electrode derived in the sample cup 244 being stored in the microprocessor's memory. The read signals derived in the wash cell 166 provides a single point calibration for relative measurement obtained in the sample cup with the microprocessor 390 comparing the readings to previous averaged readings maintained in memory for calibration signal correction, Subsequently, the microprocessor processes the obtained and stored values to derive a concentration value for the substance being measured which is output by the microprocesssor on the digital display 400.

From the above description, it will be recognized that the present invention provides an automatic determination of the concentration of substances contained within a sample in a rapid and efficient manner without the use of complicated values heretofore associated in the art. In addition, it is an important feature of the present invention that accurate measurements can be effectuated without the use of complicated thermostatic temperature control systems. This is made possible by the rapid and simple manipulation of the probe between the wash cell and unknown body fluid specimen in a single vertical axial motion which permits wash cell and body fluid measurement readings to be effectuated in close time proximity. Further, due to the relatively large thermal mass of the probe 40 compared to the extremely small volume of body fluid sample, (i.e. approximately 50 microliters), and the probe 40 being normally stored in the aqueous solution in the wash cell at ambient temperature, upon rapid immersion within the sample cup, the probe serves to immediately equalize the temperature of the body fluid specimen to the temperature of the probe, which temperature is substantially equal to the temperature of the aqueous solution within the wash cell. Due to the temperature of the calibrant solution within the wash cell being equal to the temperature of the body fluid sample when the probe is rapidly immersed in the sample, inaccuracies caused by temperature differential between the calibrant solution and specimen are eliminated. Thus, the present invention effectuates a major simplification in the prior art instrumentation, with the high thermal mass and superior thermal conductivity characteristics of the probe forming a simple means for thermally coupling the aqueous solution of the wash cell to the specimen contained within the sample cup.

In addition, it should be recognized that the only moving parts of the analyzer 10 of the present invention comprise the probe step motors 321 and fluidic pumps 352 disposed at each of the analytical modules 33a, b, c, etc. Further, the present invention permits the use of both ion selective as well as enzymatic electrodes upon the same analyzer system with the only major differences in the use of the same upon the analyzer being in computer software calculation program 510. Thus, the present invention has extremely wide potential to provide accurate analysis of varying substances of interest. Similarly, those skilled in the art will recognize that as new ionophore materials and enzyme membranes are developed, their inclusion into the ion selective and enzymatic electrodes 70a and 70b respectively can be readily accomplished to further expand the measurement potential of the analyzer 10 of the present invention.

Referring to FIGS. 26 and 27, an additional embodiment of the open ended wash cell 18 of the present invention is depicted. In this additional embodiment, the wash cell 18a includes a base plate 150a and pair of mounting apertures 202a which permit the mounting of the wash cell 18a to the analytical module 33 in an analogous manner to that previously described. Similarly, the probe 40 is axially reciprocated throughout the length of the wash cell 18a to sequentially reside within the wash cell 18a and sample cup. However, in this embodiment, the wash cell vessel 600 preferably comprises a cylindrical tubular vessel which as shown in FIG. 27 is preferably segregated by radially extending partitions 602 and 604 to define three annular chambers 606, 608 and 610. Each of the chambers 606, 608 and 610 include a reticulated foam core 612, 614 and 616 respectively. Each of the foam cores 612, 614 and 616 have a central aperture extending axially therethrough which is preferably formed to be slightly less than the diameter of the probe 40 such that during axial reciprocation of the probe within the wash cell 18a, the reticulated foam cores 612, 614 and 616 gently contact or wipe the surface of the probe. The partitions 602 and 604 and end caps 618 and 620 additionally include a central aperture extending axially therethrough which is preferably sized to be slightly greater than the diameter of the probe 40 and which serve in combination with one another in an analogous manner to the star bushing 168 of the other embodiment of the wash cell 18 so as to guide the probe 40 during axial reciprocation through the wash cell 18a.

The chambers 606 and 608 are preferably provided with an aperture 626 and 628 which are connected to an analogous fluidic pump and supply system as previously described to supply aqueous solution bearing a known concentration of the desired substance to be measured into the chambers 606 and 608. Similarly, all three of the chambers 606, 608 and 610 are preferably provided with an aperture 630, 632 and 634 respectively which are connected to a fluidic pump and vacuum system so as to withdraw fluid from each of the chambers 606, 608 and 610 respectively.

In this alternative embodiment a separate aqueous solution is preferably supplied to each of the chambers 606 and 608 such that the chamber 606 can serve as a first calibration zone or medium while the chamber 608 can serve as a second calibration zone. Thus, the probe 40 can be reciprocated axially downward from the first chamber 606 to the second chamber 608 with readings being taken in a manner previously described in each of the chambers 68 to constantly and rapidly obtain a two point calibration of the probe. The lowermost chamber 610 preferably is utilized as a drying chamber to remove any portion of the aqueous solution remaining upon the probe prior to exit of the probe from the cell toward the sample cup.

As will be recognized, in this second embodiment of the wash cell 18a, the reticulated foam inserts 612, 614, and 616 serve as a substrate or carrier for aqueous solution being circulated through the flow cell and thereby prevent any aqueous solution drooling out from the wash cell 18a. In addition, it will be recognized that if so desired, this same type of reticulated foam wash cell can be utilized in only a two cell configuration as opposed to the three cell configuration depicted, whereby only a single calibration wash chamber and drying chamber is utilized. In such a two cell embodiment, calibration of the probe would of course be effectuated in a manner previously described in relation to the wash cell embodiment 18 depicted in FIG. 4. Further, those skilled in the art will recognize that in the additional embodiment 18a of the wash cell, the previously described fluidic pump and vacuum system will need to be modified accordingly to permit the separate storage and removal of two separate aqueous solutions at each module.

Although in the preferred embodiment, certain structures, components and materials have been defined, those skilled in the art will recognize that various modifications and equivalent structures can be utilized and such modifications and equivalent structure are within the scope of the present invention and expressly contemplated herein.

What is claimed is:

1. A sample holder for use in a body fluid analyzer device, said sample holder comprising:
 a cup member having an open top and closed bottom end;
 a well formed in said cup member extending axially downward adjacent said top end toward said bottom end, said well adapted to store a body fluid sample therein; and
 a reservoir formed about said well sized to accommodate any spill over of said body fluid sample from said well;
 wherein said well includes an axially extending channel upon its inner surface.

2. The sample holder of claim 1 wherein said well is formed in a cylindrical configuration.

3. The sample cup holder of claim 1 further comprising a flange formed adjacent said bottom end of said cup member.

4. The sample cup holder of claim 3 wherein the lower end of said well is formed in a complementary configuration to the end of a probe of said analyzer device.

5. The sample holder of claim 1 wherein the upper end of said well is formed in an angularly inclined configuration.

6. The sample holder of claim 5 wherein said reservoir comprises an annular chamber extending about said well.

7. The sample holder of claim 6 wherein said well and said annular chamber are coaxially positioned within said cup member.

* * * * *